United States Patent
Auth et al.

(10) Patent No.: US 8,021,359 B2
(45) Date of Patent: *Sep. 20, 2011

(54) TRANSSEPTAL CLOSURE OF A PATENT FORAMEN OVALE AND OTHER CARDIAC DEFECTS

(75) Inventors: David C. Auth, Kirkland, WA (US); Robert L. Barry, Kirkland, WA (US); Joseph E. Eichinger, Everett, WA (US); Bryan A. Kinsella, Seattle, WA (US); Roger A. Sahm, Snohomish, WA (US); Robert S. Schwartz, Inner Grove Heights, MN (US); Robert A. Van Tassel, Exelsior, MN (US)

(73) Assignee: CoAptus Medical Corporation, Redmond, WA (US)

( * ) Notice: Subject to any disclaimer, the term of this patent is extended or adjusted under 35 U.S.C. 154(b) by 1466 days.

This patent is subject to a terminal disclaimer.

(21) Appl. No.: 10/754,790

(22) Filed: Jan. 8, 2004

(65) Prior Publication Data
US 2004/0243122 A1  Dec. 2, 2004
US 2008/0312646 A9  Dec. 18, 2008

Related U.S. Application Data

(60) Provisional application No. 60/447,760, filed on Feb. 13, 2003, provisional application No. 60/474,055, filed on May 28, 2003.

(51) Int. Cl.
*A61B 18/14* (2006.01)
(52) U.S. Cl. .............. 606/28; 606/41; 128/898

(58) Field of Classification Search .............. 606/27–52, 606/213–215; 128/898; 607/101, 102, 122
See application file for complete search history.

(56) References Cited

U.S. PATENT DOCUMENTS

| | | |
|---|---|---|
| 2,582,628 A | 1/1952 | Halloran |
| 3,862,627 A | 1/1975 | Hans, Sr. |
| 4,273,127 A | 6/1981 | Auth et al. |
| 4,492,231 A | 1/1985 | Auth |
| 4,532,924 A | 8/1985 | Auth et al. |
| 4,556,065 A | 12/1985 | Hoffmann |
| 4,799,479 A | 1/1989 | Spears |
| 4,813,926 A | 3/1989 | Kerwin |
| 4,822,348 A | 4/1989 | Casey |
| 4,832,048 A | 5/1989 | Cohen |
| 4,850,960 A | 7/1989 | Grayzel |

(Continued)

FOREIGN PATENT DOCUMENTS
WO    WO-87/04081 A1    7/1987
(Continued)

OTHER PUBLICATIONS
U.S. Appl. No. 11/004,634, Auth et al.
(Continued)

*Primary Examiner* — Michael Peffley
(74) *Attorney, Agent, or Firm* — DLA Piper LLP (US)

(57) ABSTRACT

The present invention provides for therapeutic treatment methods, devices, and systems for the partial or complete closure or occlusion of a patent foramen ovale ("PFO"). In particular, various methods, devices, and systems for joining or welding tissues, in order to therapeutically close a PFO are described. In yet another aspect of the invention, various methods, devices, and systems for the penetration of the interatrial septum enabling left atrial access are also provided.

22 Claims, 14 Drawing Sheets

U.S. PATENT DOCUMENTS

| | | |
|---|---|---|
| 4,892,098 A | 1/1990 | Sauer |
| 4,929,246 A | 5/1990 | Sinofsky |
| 5,056,517 A | 10/1991 | Fenici |
| 5,071,417 A | 12/1991 | Sinofsky |
| 5,122,137 A | 6/1992 | Lennox |
| 5,156,613 A | 10/1992 | Sawyer |
| 5,207,670 A | 5/1993 | Sinofsky |
| 5,290,272 A | 3/1994 | Burstein et al. |
| 5,290,278 A | 3/1994 | Anderson |
| 5,298,224 A | 3/1994 | Plum |
| 5,300,065 A | 4/1994 | Anderson |
| 5,334,191 A | 8/1994 | Poppas et al. |
| 5,336,221 A | 8/1994 | Anderson |
| 5,364,389 A | 11/1994 | Anderson |
| 5,405,322 A | 4/1995 | Lennox et al. |
| 5,409,479 A | 4/1995 | Dew et al. |
| 5,409,481 A | 4/1995 | Poppas et al. |
| 5,421,338 A | 6/1995 | Crowley et al. |
| 5,451,235 A | 9/1995 | Lock et al. |
| 5,454,807 A | 10/1995 | Lennox et al. |
| 5,505,730 A | 4/1996 | Edwards |
| 5,507,744 A | 4/1996 | Tay et al. |
| 5,522,873 A | 6/1996 | Jackman et al. |
| 5,540,677 A | 7/1996 | Sinofsky |
| 5,545,195 A | 8/1996 | Lennox et al. |
| 5,569,239 A | 10/1996 | Sinofsky |
| 5,571,088 A | 11/1996 | Lennox et al. |
| 5,571,216 A | 11/1996 | Anderson |
| 5,575,772 A | 11/1996 | Lennox |
| 5,584,872 A | 12/1996 | LaFontaine et al. |
| 5,611,794 A | 3/1997 | Sauer et al. |
| 5,643,171 A | 7/1997 | Bradshaw et al. |
| 5,658,280 A | 8/1997 | Issa |
| 5,662,643 A | 9/1997 | Kung et al. |
| 5,662,647 A | 9/1997 | Crow et al. |
| 5,669,934 A | 9/1997 | Sawyer |
| 5,695,493 A | 12/1997 | Nakajima et al. |
| 5,702,421 A | 12/1997 | Schneidt |
| 5,709,224 A | 1/1998 | Behl et al. |
| 5,713,891 A | 2/1998 | Poppas |
| 5,725,512 A | 3/1998 | Swartz et al. |
| 5,725,522 A | 3/1998 | Sinofsky |
| 5,725,552 A | 3/1998 | Kotula et al. |
| 5,749,895 A | 5/1998 | Sawyer et al. |
| 5,757,772 A | 5/1998 | Thornberg et al. |
| 5,782,848 A | 7/1998 | Lennox |
| 5,782,860 A | 7/1998 | Epstein et al. |
| 5,810,810 A | 9/1998 | Tay et al. |
| 5,824,015 A | 10/1998 | Sawyer |
| 5,827,265 A | 10/1998 | Glinsky et al. |
| 5,827,268 A | 10/1998 | Laufer |
| 5,865,827 A | 2/1999 | Bullister |
| 5,868,702 A | 2/1999 | Stevens et al. ............... 604/53 |
| 5,873,828 A | 2/1999 | Fujio et al. |
| 5,897,551 A | 4/1999 | Everett et al. |
| 5,919,188 A | 7/1999 | Shearon et al. |
| 5,919,191 A | 7/1999 | Lennox et al. |
| 5,919,200 A * | 7/1999 | Stambaugh et al. .......... 606/159 |
| 5,925,078 A | 7/1999 | Anderson |
| 5,928,224 A | 7/1999 | Laufer |
| 5,928,266 A | 7/1999 | Kontos |
| 5,931,165 A | 8/1999 | Reich et al. |
| 5,944,738 A | 8/1999 | Amplatz et al. |
| 5,957,919 A | 9/1999 | Laufer |
| 5,964,782 A | 10/1999 | Lafontaine et al. |
| 5,972,026 A | 10/1999 | Laufer et al. |
| 5,984,909 A | 11/1999 | Lurie et al. |
| 5,989,284 A | 11/1999 | Laufer |
| 6,004,269 A | 12/1999 | Crowley et al. |
| 6,004,316 A | 12/1999 | Laufer |
| 6,010,516 A | 1/2000 | Hulka |
| 6,033,397 A | 3/2000 | Laufer et al. |
| 6,033,398 A | 3/2000 | Farley et al. |
| 6,036,687 A | 3/2000 | Laufer et al. |
| 6,048,333 A | 4/2000 | Lennox et al. |
| 6,063,081 A | 5/2000 | Mulier et al. |
| 6,063,085 A | 5/2000 | Tay et al. |
| 6,066,126 A | 5/2000 | Li et al. |
| 6,068,653 A | 5/2000 | LaFontaine |
| 6,071,277 A | 6/2000 | Farley et al. |
| 6,071,303 A | 6/2000 | Laufer |
| 6,083,219 A | 7/2000 | Laufer |
| 6,083,223 A | 7/2000 | Baker |
| 6,083,255 A | 7/2000 | Laufer et al. |
| 6,086,586 A | 7/2000 | Hooven |
| 6,087,552 A | 7/2000 | Gregory |
| 6,091,995 A | 7/2000 | Ingle et al. |
| 6,106,520 A | 8/2000 | Laufer et al. |
| 6,128,522 A | 10/2000 | Acker et al. |
| 6,132,429 A | 10/2000 | Baker |
| 6,135,997 A | 10/2000 | Laufer et al. |
| 6,139,527 A | 10/2000 | Laufer et al. |
| 6,149,660 A | 11/2000 | Laufer et al. |
| 6,152,139 A | 11/2000 | Laufer |
| 6,156,032 A | 12/2000 | Lennox |
| 6,165,206 A | 12/2000 | Tu |
| 6,168,594 B1 | 1/2001 | LaFontaine et al. |
| 6,200,315 B1 | 3/2001 | Gaiser et al. |
| 6,200,333 B1 | 3/2001 | Laufer |
| 6,206,907 B1 | 3/2001 | Marino et al. |
| 6,210,411 B1 | 4/2001 | Hofmann et al. |
| 6,211,335 B1 | 4/2001 | Owen et al. |
| 6,221,068 B1 | 4/2001 | Fried et al. |
| 6,238,389 B1 | 5/2001 | Paddock et al. |
| 6,254,598 B1 | 7/2001 | Edwards et al. |
| 6,254,601 B1 | 7/2001 | Burbank et al. |
| 6,257,241 B1 | 7/2001 | Wampler |
| 6,258,087 B1 | 7/2001 | Edwards et al. |
| 6,273,886 B1 | 8/2001 | Edwards et al. |
| 6,273,907 B1 | 8/2001 | Laufer |
| 6,283,935 B1 | 9/2001 | Laufer et al. |
| 6,283,962 B1 | 9/2001 | Tu et al. |
| 6,283,988 B1 | 9/2001 | Laufer et al. |
| 6,283,989 B1 | 9/2001 | Laufer et al. |
| 6,290,674 B1 | 9/2001 | Roue et al. |
| 6,299,633 B1 | 10/2001 | Laufer |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,338,731 B1 | 1/2002 | Laufer et al. |
| 6,352,534 B1 | 3/2002 | Paddock et al. |
| 6,355,030 B1 | 3/2002 | Aldrich et al. |
| 6,355,031 B1 | 3/2002 | Edwards et al. |
| 6,358,245 B1 | 3/2002 | Edwards et al. |
| 6,375,615 B1 | 4/2002 | Flaherty et al. |
| 6,379,368 B1 | 4/2002 | Corcoran et al. |
| 6,383,198 B1 | 5/2002 | Hamilton |
| 6,391,048 B1 | 5/2002 | Ginn et al. |
| 6,391,049 B1 | 5/2002 | McNally et al. |
| 6,398,779 B1 | 6/2002 | Buysse et al. |
| 6,398,782 B1 | 6/2002 | Pecor et al. |
| 6,398,797 B2 | 6/2002 | Bombard et al. |
| 6,401,719 B1 | 6/2002 | Farley et al. |
| 6,401,720 B1 | 6/2002 | Stevens et al. |
| 6,419,669 B1 | 7/2002 | Frazier et al. |
| 6,438,424 B1 | 8/2002 | Knowlton |
| 6,440,128 B1 | 8/2002 | Edwards et al. |
| 6,440,152 B1 | 8/2002 | Gainor et al. |
| 6,453,202 B1 | 9/2002 | Knowlton |
| 6,461,314 B1 | 10/2002 | Pant et al. |
| 6,463,332 B1 | 10/2002 | Aldrich |
| 6,464,626 B1 | 10/2002 | Peterson |
| 6,464,689 B1 | 10/2002 | Qin et al. |
| 6,470,216 B1 | 10/2002 | Knowlton |
| 6,482,203 B2 | 11/2002 | Paddock et al. |
| 6,488,673 B1 | 12/2002 | Laufer et al. |
| 6,494,879 B2 | 12/2002 | Lennox et al. |
| 6,494,888 B1 | 12/2002 | Laufer et al. |
| 6,506,196 B1 | 1/2003 | Laufer |
| 6,520,185 B1 | 2/2003 | Bommannan et al. |
| 6,524,326 B1 | 2/2003 | Zhu et al. |
| 6,526,302 B2 | 2/2003 | Hassett |
| 6,529,778 B2 | 3/2003 | Prutchi |
| 6,547,776 B1 | 4/2003 | Gaiser et al. |
| 6,554,827 B2 | 4/2003 | Chandrasekaran et al. |
| 6,558,366 B1 | 5/2003 | Drasler et al. |
| 6,562,034 B2 | 5/2003 | Edwards et al. |

| | | |
|---|---|---|
| 6,562,037 B2 | 5/2003 | Paton et al. |
| 6,562,052 B2 | 5/2003 | Nobles et al. |
| 6,565,557 B1 | 5/2003 | Sporri et al. |
| 6,575,971 B2 | 6/2003 | Hauck et al. |
| 6,577,902 B1 | 6/2003 | Laufer et al. |
| 6,583,117 B2 | 6/2003 | Owen et al. |
| 6,589,238 B2 | 7/2003 | Edwards et al. |
| 6,595,934 B1 | 7/2003 | Hissong et al. |
| 6,602,251 B2 | 8/2003 | Burbank et al. |
| 6,605,084 B2 | 8/2003 | Acker et al. |
| 6,606,513 B2 | 8/2003 | Lardo et al. |
| 6,613,047 B2 | 9/2003 | Edwards |
| 6,629,534 B1 | 10/2003 | St. Goar et al. ............... 128/898 |
| 6,629,951 B2 | 10/2003 | Laufer et al. |
| 6,635,052 B2 | 10/2003 | Loeb |
| 6,635,054 B2 | 10/2003 | Fjield et al. |
| 6,645,198 B1 | 11/2003 | Bommannan et al. |
| 6,663,622 B1 | 12/2003 | Foley et al. |
| 6,663,639 B1 | 12/2003 | Laufer et al. |
| 6,669,655 B1 | 12/2003 | Acker et al. |
| 6,669,687 B1 | 12/2003 | Saadat |
| 6,672,312 B2 | 1/2004 | Acker |
| 6,673,070 B2 | 1/2004 | Edwards et al. |
| 6,676,685 B2 | 1/2004 | Pedros et al. |
| 6,699,243 B2 | 3/2004 | West et al. |
| 6,702,835 B2 | 3/2004 | Ginn |
| 6,706,039 B2 | 3/2004 | Mulier et al. |
| 6,712,074 B2 | 3/2004 | Edwards et al. |
| 6,712,814 B2 | 3/2004 | Edwards et al. |
| 6,719,770 B2 | 4/2004 | Laufer et al. |
| 6,723,092 B2 | 4/2004 | Brown et al. |
| 6,728,565 B2 | 4/2004 | Wendlandt |
| 6,733,495 B1 | 5/2004 | Bek et al. |
| 6,733,498 B2 | 5/2004 | Paton et al. |
| 6,775,575 B2 | 8/2004 | Bommannan et al. |
| 6,776,784 B2 | 8/2004 | Ginn |
| 6,782,565 B2 | 8/2004 | Hinton |
| 6,783,523 B2 | 8/2004 | Qin et al. |
| 6,790,207 B2 | 9/2004 | Utley et al. |
| 6,802,841 B2 | 10/2004 | Utley et al. |
| 6,821,285 B2 | 11/2004 | Laufer et al. |
| 6,827,713 B2 | 12/2004 | Bek et al. |
| 6,836,688 B2 | 12/2004 | Ingle et al. |
| 6,852,108 B2 | 2/2005 | Barry et al. |
| 6,866,663 B2 | 3/2005 | Edwards et al. |
| 6,875,171 B2 | 4/2005 | Paolitto et al. |
| 6,887,238 B2 | 5/2005 | Jahns et al. |
| 6,939,348 B2 * | 9/2005 | Malecki et al. ................ 606/41 |
| 2001/0051800 A1 | 12/2001 | Eugeny et al. |
| 2002/0042564 A1 | 4/2002 | Cooper et al. |
| 2002/0068932 A1 | 6/2002 | Edwards et al. |
| 2002/0082621 A1 | 6/2002 | Schurr et al. |
| 2002/0091379 A1 | 7/2002 | Danek et al. |
| 2002/0095164 A1 | 7/2002 | Andreas et al. |
| 2002/0107512 A1 | 8/2002 | Edwards |
| 2002/0107531 A1 | 8/2002 | Schreck et al. |
| 2002/0128672 A1 | 9/2002 | Dinger et al. |
| 2002/0143324 A1 | 10/2002 | Edwards |
| 2002/0151871 A1 | 10/2002 | Gaiser et al. |
| 2002/0169377 A1 | 11/2002 | Khairkhahan et al. |
| 2002/0183787 A1 | 12/2002 | Wahr et al. |
| 2002/0183789 A1 | 12/2002 | Neev |
| 2002/0193787 A1 | 12/2002 | Qin et al. |
| 2002/0193816 A1 | 12/2002 | Laufer et al. |
| 2003/0009194 A1 | 1/2003 | Saker et al. |
| 2003/0024538 A1 | 2/2003 | Edwards et al. |
| 2003/0028188 A1 | 2/2003 | Paddock et al. |
| 2003/0028189 A1 | 2/2003 | Woloszko et al. |
| 2003/0050632 A1 | 3/2003 | Fjield et al. |
| 2003/0069570 A1 | 4/2003 | Witzel et al. |
| 2003/0078578 A1 | 4/2003 | Truckai et al. |
| 2003/0092689 A1 | 5/2003 | Escandon et al. |
| 2003/0093071 A1 | 5/2003 | Hauck et al. |
| 2003/0130730 A1 | 7/2003 | Cohn et al. |
| 2003/0135206 A1 | 7/2003 | Edwards et al. |
| 2003/0144652 A1 | 7/2003 | Baket et al. |
| 2003/0144694 A1 | 7/2003 | Chanduszko et al. |
| 2003/0158551 A1 | 8/2003 | Paton et al. |
| 2003/0178032 A1 | 9/2003 | Ingle et al. |
| 2003/0191511 A1 | 10/2003 | Laufer et al. |
| 2003/0191512 A1 | 10/2003 | Laufer et al. |
| 2003/0195511 A1 | 10/2003 | Barry |
| 2003/0195593 A1 | 10/2003 | Ingle et al. |
| 2003/0195604 A1 | 10/2003 | Ingle et al. |
| 2003/0208232 A1 | 11/2003 | Blaeser et al. |
| 2004/0003819 A1 | 1/2004 | St. Goar et al. |
| 2004/0039312 A1 | 2/2004 | Hillstead et al. |
| 2004/0059347 A1 | 3/2004 | Hamilton |
| 2004/0143294 A1 | 7/2004 | Corcoran et al. |
| 2004/0176752 A1 | 9/2004 | Alfano et al. |
| 2004/0193147 A1 | 9/2004 | Malecki et al. |
| 2004/0230185 A1 | 11/2004 | Malecki et al. |
| 2004/0267191 A1 | 12/2004 | Gifford et al. |
| 2005/0021016 A1 | 1/2005 | Malecki et al. |
| 2005/0033288 A1 | 2/2005 | Auth et al. |
| 2005/0034735 A1 | 2/2005 | Deem et al. |
| 2005/0055050 A1 | 3/2005 | Alfaro |
| 2005/0065506 A1 | 3/2005 | Phan |
| 2005/0070923 A1 | 3/2005 | McIntosh |
| 2005/0080406 A1 | 4/2005 | Malecki et al. |
| 2005/0131401 A1 | 6/2005 | Malecki et al. |
| 2005/0131460 A1 | 6/2005 | Gifford et al. |
| 2005/0192627 A1 | 9/2005 | Whisenant et al. |
| 2005/0192654 A1 | 9/2005 | Chanduszko et al. |
| 2005/0228283 A1 | 10/2005 | Gifford et al. |
| 2005/0267464 A1 | 12/2005 | Truckai et al. |
| 2005/0267523 A1 | 12/2005 | Devellian et al. |
| 2005/0267524 A1 | 12/2005 | Chanduszko |
| 2005/0267525 A1 | 12/2005 | Chanduszko |
| 2005/0267526 A1 | 12/2005 | Wahr et al. |
| 2006/0009800 A1 | 1/2006 | Christianson et al. |
| 2006/0036282 A1 | 2/2006 | Wahr et al. |
| 2006/0036284 A1 | 2/2006 | Blaeser et al. |
| 2006/0074410 A1 | 4/2006 | Malecki et al. |

FOREIGN PATENT DOCUMENTS

| | | |
|---|---|---|
| WO | WO-97/32532 | 9/1997 |
| WO | WO-98/38936 | 9/1998 |
| WO | WO-99/18826 | 4/1999 |
| WO | WO-99/18862 | 4/1999 |
| WO | WO-99/18864 | 4/1999 |
| WO | WO-99/18870 | 4/1999 |
| WO | WO-99/18871 | 4/1999 |
| WO | WO-99/32040 | 7/1999 |
| WO | WO-99/34741 | 7/1999 |
| WO | WO-99/42044 | 8/1999 |
| WO | WO-99/42045 | 8/1999 |
| WO | WO-00/18307 | 4/2000 |
| WO | WO-00/18308 | 4/2000 |
| WO | WO-00/51510 | 9/2000 |
| WO | WO-00/57495 | 9/2000 |
| WO | WO-00/64387 | 11/2000 |
| WO | WO-00/66006 | 11/2000 |
| WO | WO-00/66015 | 11/2000 |
| WO | WO-00/66018 | 11/2000 |
| WO | WO-00/66019 | 11/2000 |
| WO | WO-00/66021 | 11/2000 |
| WO | WO-00/66052 | 11/2000 |
| WO | WO-01/10314 | 2/2001 |
| WO | WO 01/17450 | 3/2001 |
| WO | WO-02/24092 | 3/2002 |
| WO | WO-02/058780 | 8/2002 |
| WO | WO-02/060523 A2 | 8/2002 |
| WO | WO-02/060523 A3 | 8/2002 |
| WO | WO-02/067798 | 9/2002 |
| WO | WO-2004/043266 A2 | 5/2004 |
| WO | WO-2004/069055 A2 | 8/2004 |

OTHER PUBLICATIONS

U.S. Appl. No. 11/243,324, Barry.
U.S. Appl. No. 60/474,055, Auth et al.
U.S. Appl. No. 60/477,760, Auth et al.
Caceci, Dr. Thomas, Text on Skeletal Muscle and Collagen Remodeling (10 Pages).
Chapter 6: Percutaneous Closure of Heart Defects, 2002, Health Research International (3 Pages).

Chatterjee, T. et al., "Nonsurgical Closure of Secundum Atrial Septal Defect and Patent Foremen Ovale," J Clin Basic Cardiol 4:35, 2001, Bern, Switzerland (4 Pgs.).

ConMed Corporation, "Suction Instruments & Tubing," (6 Pgs.).

Gifford, H. et al., "Methods and Apparatus for Treatment of patent Foramen Ovale," http://www.freshpatents.com/Methods-and-apparatus-for-treatment-of-patent-foramen-ovale-dt20050616plan20050131460.php, Internet pp. 1-2, Jul. 18, 2005.

Harper, R. et al., "Closure of Secundum Atrial Septal Defects With the Amplatzer Septal Occluder Device: Techniques and Problems," Catheterization and Cardiovascular Interventions, 2002, pp. 508-524, vol. 57, Wiley-Liss, Inc.

Johnston, J. H. et al., "Experimental Comparison of Endoscopic Yttrium-Aluminum-Garnet Laser, Electrosurgery, and Heater Probe for Canine Gut Arterial Coagulation: Importance of Compression and Avoidance of Erosion," Gastroenterology, 1987, pp. 1101-1108, vol. 92, No. 5, American Gastroenterological Association.

Karttunen, V. et al., "Ear Oximetry: A Noninvasive Method for Detection of Patent Foramen Ovale, A Study Comparing Dye Dilution Method and Oximetry With Contrast Transesophageal Echocardiography," Stroke, Feb. 2001, vol. 32, pp. 448-453, American Heart Association, Inc.

Kerut, E. et al., "Patent Foramen Ovale: A Review of Associated Conditions and the Impact of Physiological Size," Journal of the American College of Cardiology, Sep. 2001, pp. 613-623, vol. 38, No. 3, Elsevier Science, Inc.

Knebel, F., "Percutaneous Closure of Interatrial Communications in Adults-Prospective Embolism Prevention Study With Two and Three Dimensional Echocardiography," Cardiovascular Ultrasound, May 19, 2004, 2:5, (10 Pages).

Kramer, P., "The Hidden Connection," Endovascular Today, May 2004, pp. 47-52.

Lipton, R. et al., "Epidemiology and Economic Impact of Migraine," www.medscape.com/viewarticle/429665 <http://www.medscape.com/viewarticle/429665>, Curr Med Res Opin, 2001, 17(1s):s4-s12, Medscape.

Madison Skin & Laser Center, Thermalift™ Pre-Treatment Instructions & Thermalift™ Discharge Instructions. (2 Pages).

Malecki, W. et al., "Energy Based Devices and Methods for Treatment of Anatomic Tissue Defects," http://www.freshpatents.com/Energy-based-devices-and-methods-for-treatment-of-anatomic-tissue-defects-dt20050616ptan20050131401.php, Internet pp. 1-2, Jul. 18, 2005.

Malis, L, "Electrosurgery," J. Neurosurg., Nov. 1996, pp. 970-975, vol. 85.

Marshall, A. et al., "Structural and Compliant Anatomy of the Patent Foramen Ovale in Patients Undergoing Transcatheter Closure," American Heart Journal, Aug. 2000, pp. 303-307, vol. 140, No. 2, © Mosby, Inc.

Mayo Clinic, "Patent foremen Ovale: Paradoxical Embolism, and Paradoxical Data," Mayo Clinic Proceedings, Jan. 2004, pp. 15-20, vol. 79, No. 1, Mayo Foundation for Medical Education and Research.

McClurken, M. et al., Collagen Shrinkage and Vessel Sealing, TissueLink Medical, Inc., Technical Brief #300, TissueLink, Dover, NH.

McClurken, M. et al., "Thermal Effect of Tissue Link™ Technology on liver," TissueLink Medical, Inc., Technical Brief #301, TissueLink, Dover, NH.

McMahon, C.J. et al., "Use of the Transseptal Puncture in Transcatheter Closure of Long Tunnel-Type Patent Foramen Ovale," Heart, Aug. 2002, 88:e3, (2 Pages).

Meier, B. et al., "Contemporary Management of Patent Foramen Ovale," Circulation, Jan. 7/14, 2003, pp. 5-9, American Heart Association.

Meier, B., "Patent Foramen Ovale-Bearty Spot or Health Threat," CardiologyRounds, pp. 1-8, vol. 5, Issue 10, Dec. 2001, Brigham and Women's Hospital, Boston, Massachusetts.

Nkomo, V., et al. "Patent Foramen Ovale Transcatheter Closure Device Thromboisis," Mayo Clin Proc., Oct. 2001, pp. 1057-1061, vol. 76, © Mayo Foundation for Medical Education and Research.

NMT Medical, Inc. Brochure, "Cardioseal Septal Occlusion Systems," ML-0038.00, www.nmtmedical.com <http://www.nmtmedical.com>, Boston, MA (2 Pages).

NMT Medical, Inc. Brochure, "PFO Closure: Outcomes and Device Design Frequesently Asked Questions," ML-0116.00, pp. 1-4, www.nmtmedical.com <http://www.nmtmedical.com>, Boston, MA.

Overell, J.R. et al., "Interatrial Septal Abnormabilites and Stroke," Neurology, Oct. (2 of 2), 2000, vol. 55, pp. 1172-1179, © AAN Enterprises.

Patent Foramen Ovale [PFO], (1 Page).

Rosenbaum, M. et al., "An Exploratory Investigation of the Morphology and Biochemistry of Cellulite," Journal of the American Society of Plastic Surgeons, Jun. 1993, pp. 1934-1939, vol. 101, Issue 7, Lippincott,Willams & Wdkins. (Abstract Provided—2 Pages).

Ruiz, C. et al., "The Puncture Technique: A New Method for Transcatheter Closure of Patent Foramen Ovale," Catheterization and Cardiovascular Interventions, 2001, pp. 369-372, vol. 53, Wiley-Liss, Inc.

Schuchlenz, H. et al., "Transesophageal Echocardiography For Quantifying Size of Patent Foramen Ovale in patients With Cryptogenic Cerebrovascular Events," Stroke, Jan. 2003, p. 293-296, American Heart Association.

Schwerzmann, M. et al., "Percutaneous Closure of Patent Foramen Ovale Reduces the Frequency of Migraine Attacks," Neurology, Apr. (2 of 2), 2004, pp. 1399-1401, vol. 62, AAN Enterprises, Inc.

Shepard, S., "TissueLink's Hemostasis Device Stirs Interest of Local Surgeons," TissueLink, Nov. 7, 2003, Print Edition (3 Pages).

Silverglide, Surgical Technologies. inc., "What Makes SILVERGlide Non-Stick Bipolar Forceps Different" (1 Page).

Stuart, M., "Stroke Prevention: The Newest Frontier in Interventional Cardiology," Interventional Cardiology, Oct. 2003, p. 23-28, Windhover Information Inc.

Szili-Torok, T. et al., "Transseptal Left Heart Catheterisation Guided by Intracardiac Echocardiography," Heart, 2001, 86:e11, Dept. of Cardiology, Rotterdam, The Netherlands. (5 Pages).

The Thermage Procedure Brochure. (2 Pages).

Walsh, K.P. et al., "Transcatheter closure of patent foramen ovale Using the Amplatzer Septal Occluder to Prevent Recurrence of Neurological Decompression Illness in Divers," Heart 1999, pp. 257-261, vol. 81.

Wright, N. et al., "Denaturation of Collagen via Heating: An Irreversible Rate Process," Annual Review of Biomedical Engineering, 2002, pp. 109-128, vol. 4.

* cited by examiner

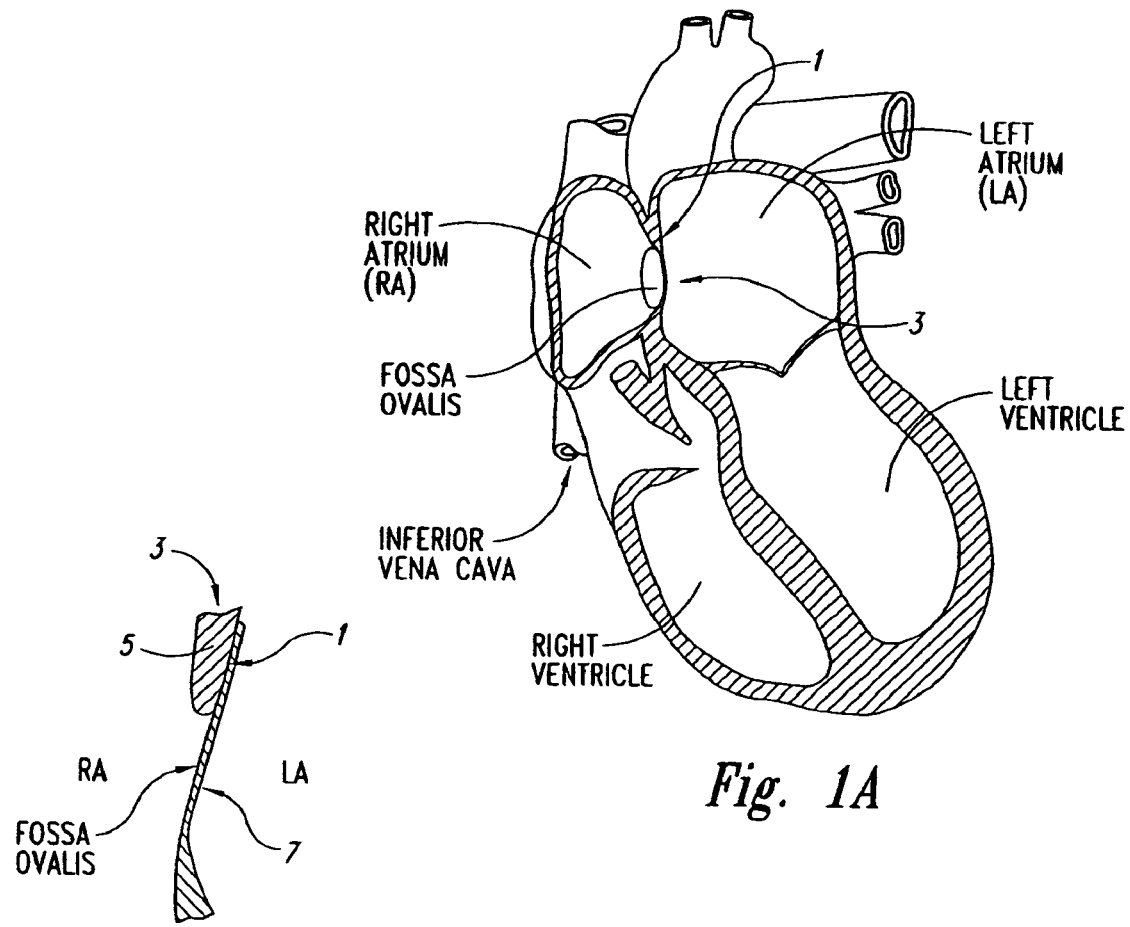
Fig. 1A
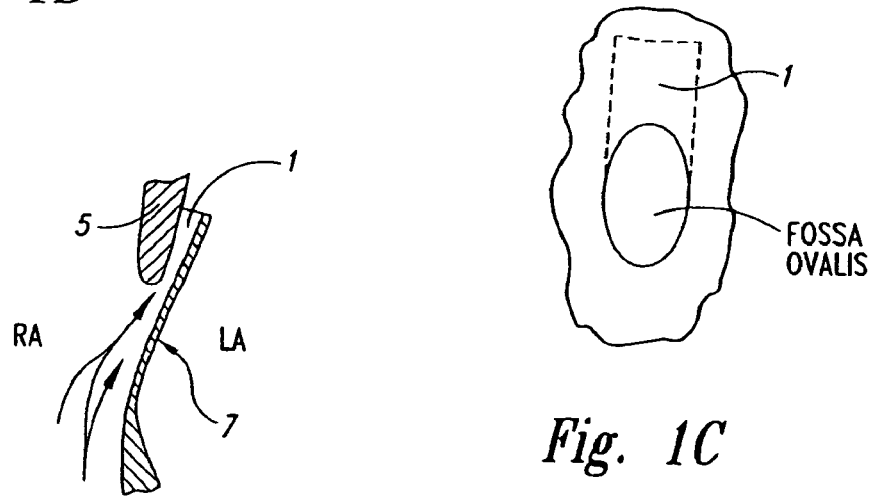
Fig. 1B
Fig. 1C
Fig. 1D

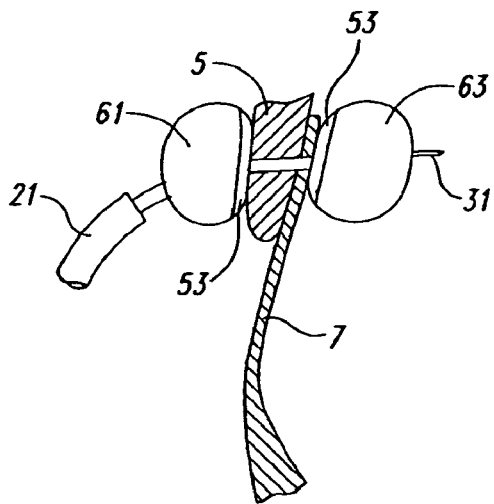
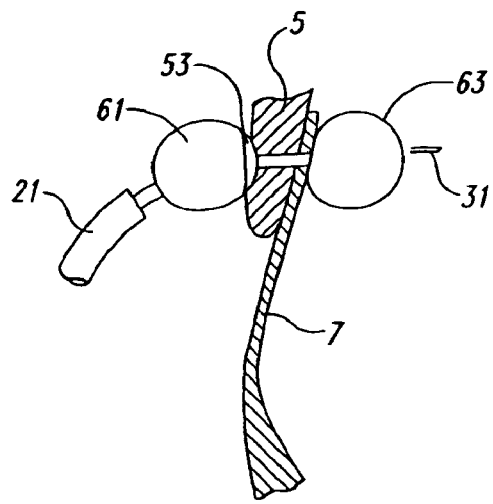
Fig. 6A    Fig. 6B
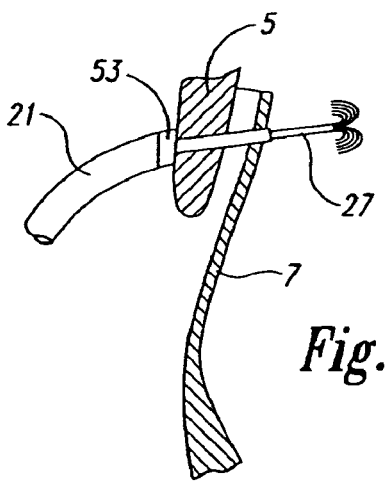
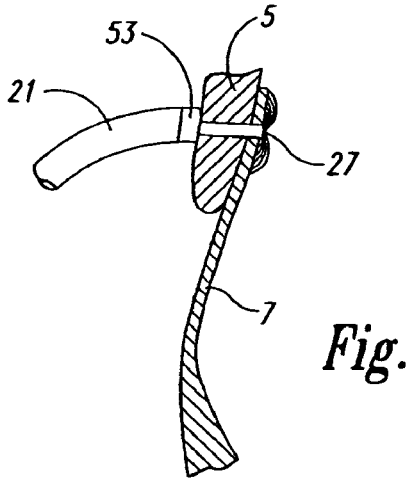
Fig. 7A    Fig. 7B
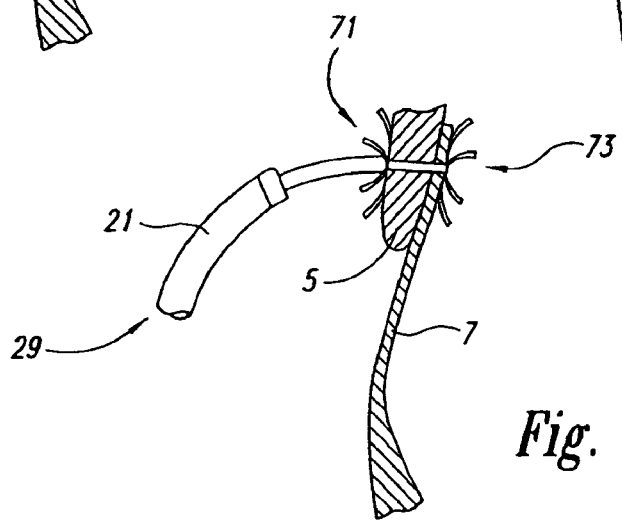
Fig. 8

 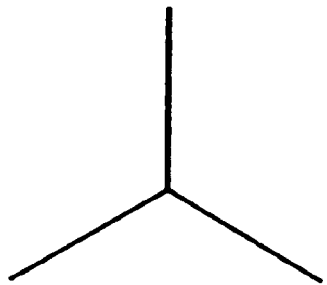 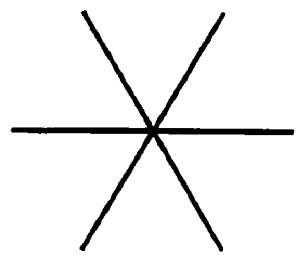
Fig. 15A　　　Fig. 15B　　　Fig. 15C
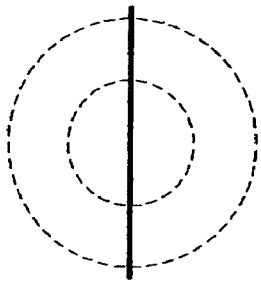 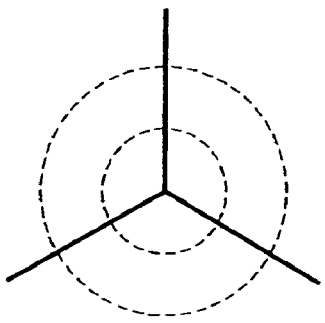 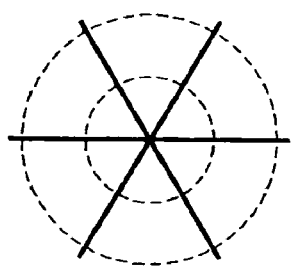
Fig. 16A　　　Fig. 16B　　　Fig. 16C
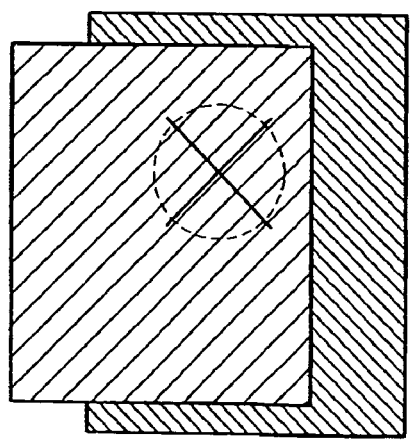
Fig. 17

①
TRANSSEPTAL
APPROACH

②
TRANSSEPTAL
PUNCTURE

ELECTRODES
DEPLOYED

③

④
ENERGIZED/CUTTING
SEPTUM

SINGLE
SLIT

TRIFURCATING
SLIT

QUAD

② SUCTION APPLIED

③ CUTTER APPLIED UNDER SUCTION (KNIFE BLADES, RF ELECTRODES, ETC.)

④ SUCTION RELEASED

SINGLE SLIT SEALING BY CIRCULAR PATTERN

SEALING/CAUTERY RINGS 1, 2, OR MORE

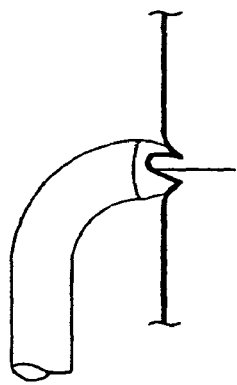
Fig. 22A ELECTRODES ACROSS, STORED
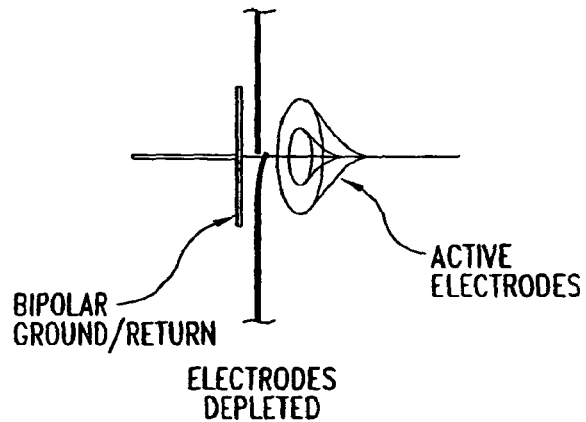
Fig. 22B ELECTRODES DEPLETED
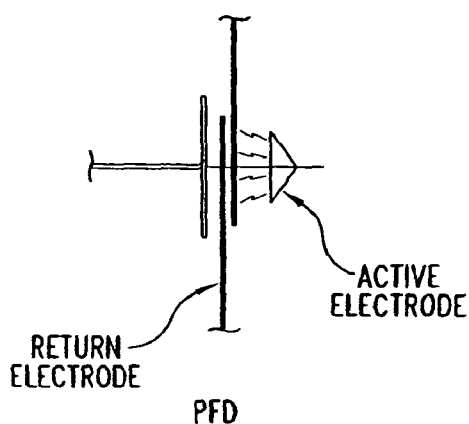
Fig. 22C PFD
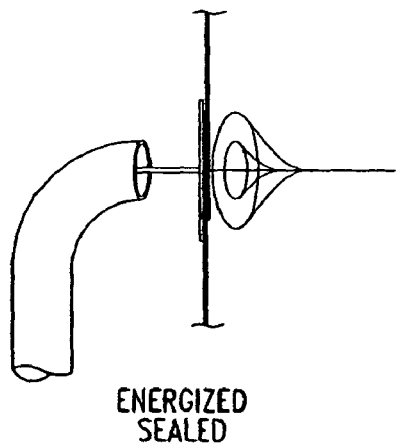
Fig. 22D ENERGIZED SEALED
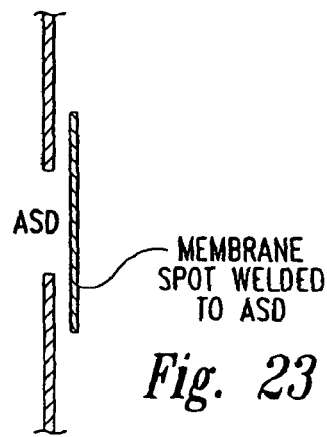
Fig. 23 ASD — MEMBRANE SPOT WELDED TO ASD

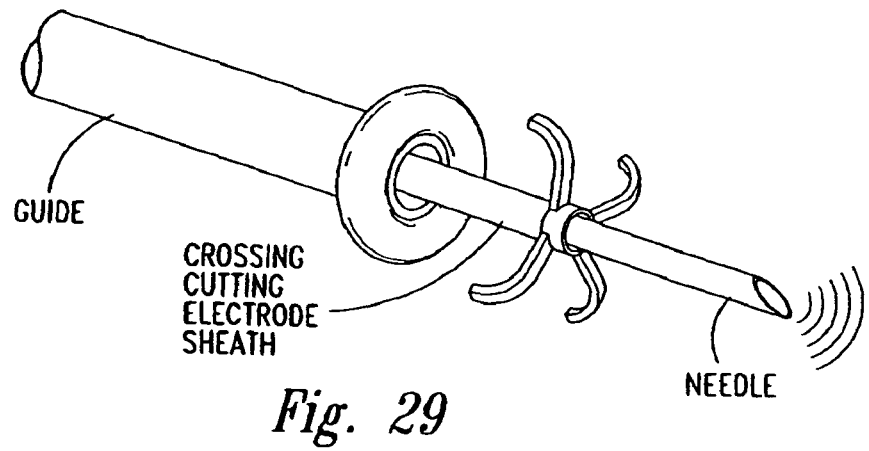
Fig. 29
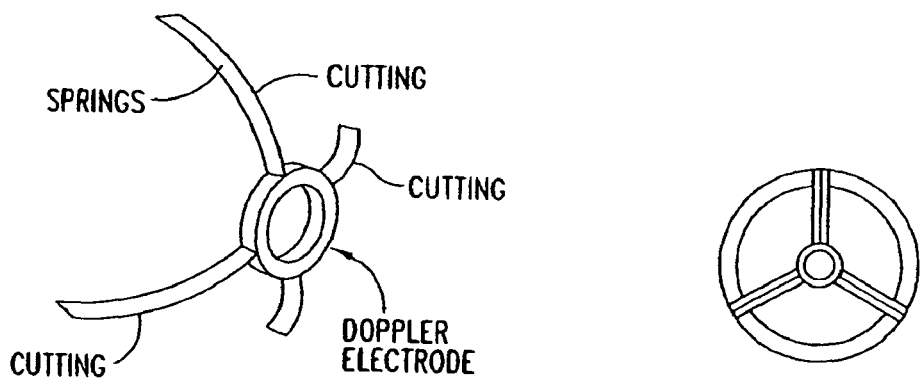
Fig. 30A
Fig. 30B
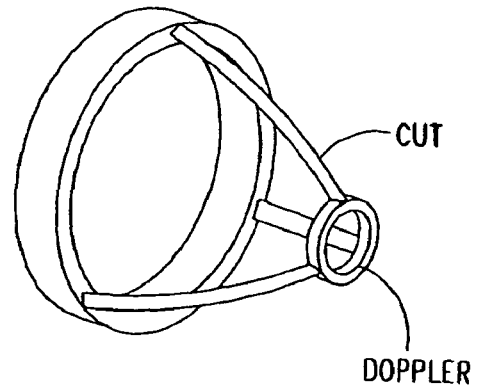
Fig. 30C

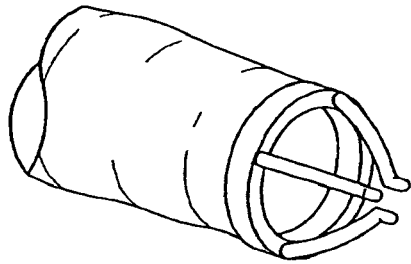
*Fig. 31A*
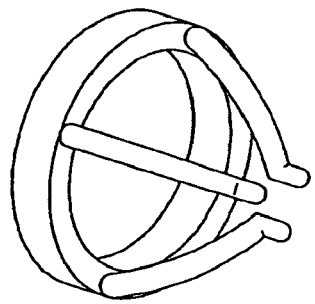
*Fig. 31B*
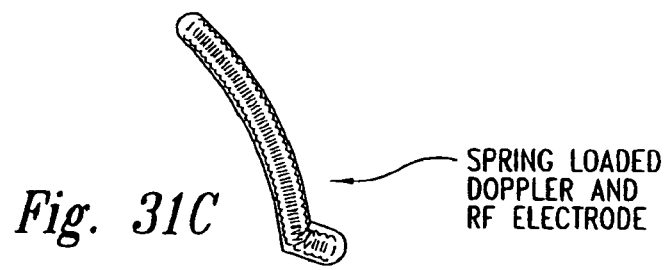
*Fig. 31C* — SPRING LOADED DOPPLER AND RF ELECTRODE
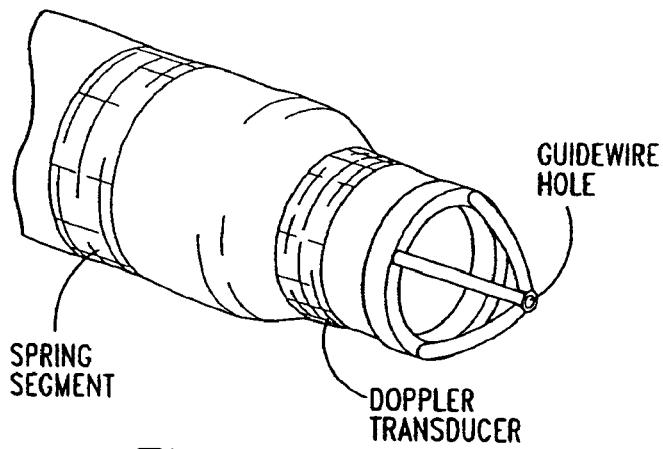
*Fig. 32A* — SPRING SEGMENT, DOPPLER TRANSDUCER, GUIDEWIRE HOLE
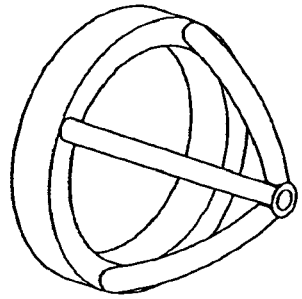
*Fig. 32B*
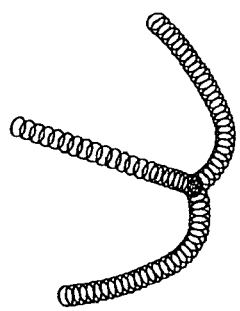
*Fig. 32C*

TRANSSEPTAL CLOSURE OF A PATENT FORAMEN OVALE AND OTHER CARDIAC DEFECTS

CROSS-REFERENCE TO RELATED APPLICATIONS

This application claims the benefit of U.S. Provisional Application No. 60/447,760, filed Feb. 13, 2003, and U.S. Provisional Application No. 60/474,055, filed May 28, 2003, both of which are incorporated herein in their entireties by reference.

COPYRIGHT NOTICE

A portion of this patent document contains material that is subject to copyright protection. The copyright owner does not object to the facsimile reproduction of the patent document as it appears in the U.S. Patent and Trademark Office patent file or records but otherwise reserves all copyright rights whatsoever.

FIELD OF THE INVENTION

The present invention relates generally to the field of cardiology, and in particular to methods, devices, and systems to close or occlude a patent foramen ovale or "PFO."

BACKGROUND OF THE INVENTION

A closed foramen ovale is formed after birth when two fetal structures, the septum secundum ("secundum") and septum primum ("primum"), become fused and fibrose together. Usually, the fusion of these two anatomical structures occurs within the first two years of life ensuring the formation of a normal functioning heart. However, in about 25-27% of the general population, the secundum and the primum either do not fuse or the fusion is incomplete. As a result, a long tunnel-like opening will exist in the interatrial septum ("septum") which allows communication between the right and left atrial chambers of the heart. This tunnel-like opening is a cardiac defect known as a PFO.

Normally, a PFO will be found near the fossa ovalis, an area of indentation on the right atrial side of the interatrial septum as illustrated in FIGS. 1A and 1B. In most circumstances, a PFO will remain functionally closed or "competent" and blood flow through the PFO will not occur due to the higher atrial pressures in the left atrium that serve to secure the flap-like primum against the secundum and interatrial septum, thereby closing the PFO. See FIGS. 1A and 1B. Nevertheless, in instances of physical exertion or when pressures are greater in the right atrium, inappropriate right-to-left shunting of blood can occur introducing venous blood and elements, such as clots or gas bubbles within the blood, into the left atrium and the systemic atrial system, posing serious health risks including: hemodynamic problems; cryptogenic strokes; venous-to-atrial gas embolism; migraines; and in some cases even death.

Traditionally, open chest surgery was required to suture or ligate closed a PFO. However, these procedures carry high attendant risks such as postoperative infection, long patient recovery, and significant patient discomfort and trauma. Less invasive, or minimally invasive, treatments are preferred and are currently being developed.

To date, most of these non-invasive, or minimally invasive, procedures involve the transcatheter implantation of various mechanical devices to close or occlude a PFO. See FIGS. 2A and 2B. That they are not well suited or designed for the long tunnel-like anatomical shape of a PFO, is a significant drawback of many PFO devices currently on the market including: the Cardia® PFO Closure Device, Amplatzer® PFO Occluder, and CardioSEAL® Septal Occlusion Device, just to name a few. As a result, device deformation and distortion is not uncommon and instances of mechanical failure, migration or even device dislodgement have been reported. Further, these devices can irritate the cardiac tissues at, or near, the implantation site, which in turn can potentially cause thromboembolic events, palpitations, and arrhythmias. Other reported complications include weakening, erosion, and tearing of the cardiac tissues around the implanted devices.

Yet another disadvantage of these mechanical devices is that the occlusion of the PFO is not instantaneous or complete immediately following implantation. Instead, occlusion and complete PFO closure requires subsequent endothelization of these devices. This endothelization process can be very gradual and can take several months or more to occur. Thus, "occlusion" of the PFO is not immediate but can be a rather slow and extended process.

Finally, the procedure to implant these devices can be technically complicated and cumbersome, requiring multiple attempts before the device can be appropriately and sufficiently delivered to the PFO. Accordingly, use of these devices may require long procedure times during which the patient must be kept under conscious sedation posing further risks to patients.

In light of these potentially serious drawbacks, new and improved non-invasive and/or minimally invasive methods, devices, and systems for the treatment of PFO, which either do not require the use of implantable devices or overcome some of the current shortcomings discussed above, are needed. The present invention meets these, as well as other, needs.

SUMMARY OF THE INVENTION

The present invention is directed to methods, devices, and systems for applying energy to join tissues, and in particular for joining the two flap-like tissues, the secundum and primum, that comprise a PFO. Tissues and blood in the human body demonstrate several unique properties when heated; accordingly heat can be used as an effective means for inducing the joining of tissues. Typically, when biological tissues and blood are heated, denaturation, melting, and/or coagulation of tissue and blood proteins, including collagen, takes place, along with the disruption of the cells and cellular walls, allowing intra-and-intercellular fluids and proteins to mix and form a type of "biological glue" which can be used to join tissues together. Yet another response to heat includes the activation of the body's healing mechanisms, which includes the activation of platelets, thrombin, fibrin, etc., and the formation of new scar tissue connections, which serve to join tissues.

A first aspect of the invention provides for methods, devices, and systems for joining tissue structures, and in particular, for joining the secundum and the primum to close or occlude a PFO. In accordance with this aspect of the invention, one method involves coapting the secundum and primum between one or more members and delivering therapeutic amounts of energy in order to join the two tissue structures together. As used herein, "coapt" means the drawing together of separated tissues or other structures. Energy sufficient to raise the native tissue temperatures of the coapted tissues to about 50°-100° C. is applied to the secundum and the primum. In accordance with this first aspect of the invention, various catheters for coapting and joining the primum and secundum are provided and further described herein.

In a second and related aspect of the invention, the primum and secundum are joined at one or more tissue contact sites, or alternatively are joined along a seam. Depending on the technique employed, complete or partial PFO closure can be selectively achieved. Described herein are possible implementations and configurations of heat generating members for creating: (1) a single tissue contact site; (2) a pattern of contact sites forming a seam; or (3) continuous seams having different shapes, for example, circular, curvilinear or straight seams.

A third aspect of the invention provides different methods, devices, and systems for ensuring tight joining of the tissues involving a welding technique. As used herein, "welding" refers to the use of heat in conjunction with pressure (as opposed to heat only) to join tissues together. Energy sufficient to raise the native tissue temperatures to about 50°-100° C. is applied in order to affect tissue welding of the secundum and the primum. Preferably, compressive force is used to not only coapt the primum and the secundum, but also to ensure the efficient and secure tissue welding during heating or energy delivery. To efficiently weld the primum and secundum, the two tissues should be encased between two opposed members that are provided as means to compress the tissues in question. Describe herein are methods and devices including various inflation members and other like devices for encasing, coapting, and compressing the tissue to be welded. As will be better understood in reference to the description provided below, one method for encasing the primum and the secundum between two opposed members is to transseptally deploy and position the two opposed members. As used herein "transseptal" means across or to the other side of the interatrial septum of the heart.

A fourth aspect involves various methods, devices, and systems for transseptally deploying various heating members, compressive members, or other like structures. In accordance with this aspect of the invention, one method involves puncturing the interatrial septum and a creating a passage therethrough so that one or more compressive members, heating members, or any combination thereof, which located at a distal working end of a PFO treatment catheter or catheter assembly, can be passed from one atrium of the heart to the other, preferably from the right to the left atrium.

A fifth aspect of the invention involves various medical kits comprising one or more catheters, puncturing means, guidewires, and/or other related components for therapeutically joining tissues or welding tissues in order to close or occlude a PFO in accordance with the present invention.

A sixth aspect of the invention involves various medical kits comprising one or more catheters, tissue penetrating devices, and other like means for transseptal penetration of the interatrial septum, thus allowing left atrial access. These devices and catheters embody various techniques and other aspects for easily identifying, positioning, and penetrating the septum at a pre-determined location.

A seventh aspect involves methods, devices, and systems for the deployment and implantation of various mechanical devices that represent an improvement over PFO occlusion devices and techniques currently known to those skilled in the art. In a related embodiment, these various devices and implants can be heated fixed or secured inside the patient.

A further aspect of the invention involves the various forms of energy that can be used to affect joining or welding of tissues, including, but not limited to: high intensity focused or unfocused ultrasound; direct heat; radiofrequency (RF); chemically induced heat (as in exothermic reactions), and other types of electromagnetic energy of differing frequencies, such as light (coherent and incoherent), laser, and microwaves can also be used. As described below, tissue heating in accordance with the present invention is char-free and controlled to prevent unintended thermal injury to the surrounding and adjacent cardiac tissues. One or more monitoring methods, devices (such as thermosensors), and systems are provided to ensure controlled and selective tissue heating.

Further understanding of the nature and advantages of the invention may be realized by reference to the remaining portions of the specification and the drawings.

BRIEF DESCRIPTION OF THE DRAWINGS

FIGS. 1A-1D illustrate a heart comprising a PFO, wherein:
FIG. 1A is a cross sectional view of a human heart;
FIG. 1B is a partial, cross-sectional view of an interatrial septum comprising a closed PFO;
FIG. 1C is a partial, cut-away, orthogonal view of the fossa ovalis and the PFO wherein the PFO is shown in phantom;
and
FIG. 1D is a partial, cross-sectional view of the interatrial septum comprising an open PFO.
FIGS. 4A-4B illustrate a PFO treatment catheter in accordance with the present invention wherein:
FIG. 4A is a perspective view;
and
FIG. 4B is a cross-sectional view of one possible implementation of the distal working end of the PFO treatment catheter shown in FIG. 4A.
FIG. 5A-5B are cross-sectional view of a interatrial septum comprising a PFO, wherein:
FIG. 5A is a partial, cross-sectional view of the interatrial septum illustrating the preferred region of penetration at a location where the secundum and primum overlap;
and
FIG. 5B is a partial, cross-sectional view of the interatrial septum illustrating the transseptal deployment of two opposed members.
FIG. 6A-6B illustrates one embodiment of a PFO treatment catheter in accordance with the present invention wherein:
FIG. 6A illustrates a PFO treatment catheter wherein the two opposed member comprise two inflation members comprising one or more RF electrodes;
and
FIG. 6B illustrates yet another embodiment of the PFO treatment catheter shown in FIG. 6A.
FIGS. 7A-7B illustrate yet another embodiment of the present invention wherein PFO treatment catheter comprises a deployable wire assembly.
FIG. 8 illustrates yet another embodiment of a PFO treatment catheter in accordance with the present invention.

FIG. 13A is a cross-sectional view illustrating the deployment of the hook-and-twist device within the PFO tunnel; and FIGS. 13B-13E are top views illustrating a method of implanting the hook-and-twist device inside the PFO tunnel.

FIGS. 15A-32C illustrate further embodiments associated with U.S. Application Nos. 60/447,760 and 60/474,055, both of which are incorporated herein by reference.

DETAILED DESCRIPTION OF THE PRESENT INVENTION

Figure 2:
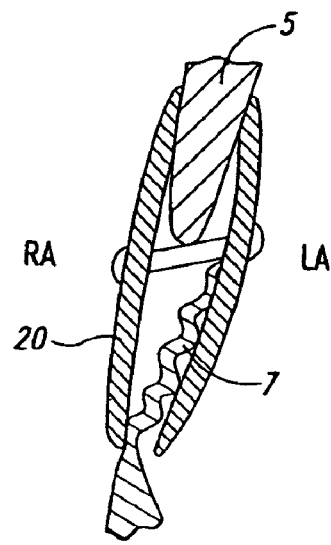
FIG. 2 illustrates the deployment of prior art mechanical occlusive devices inside the tunnel-like opening of a PFO, i.e. "PFO tunnel.
Figure 3:
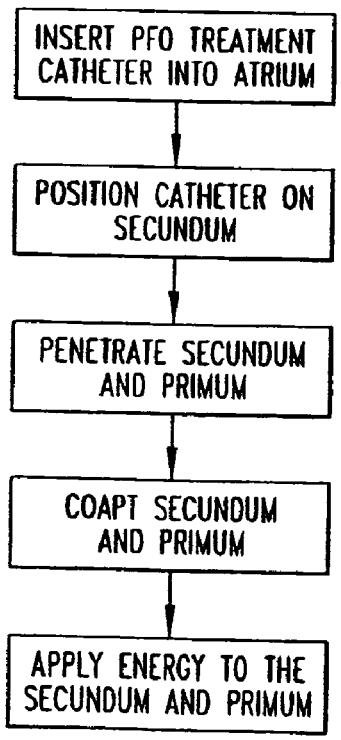
"
FIG. 3 is a flow chart illustrating a general treatment method in accordance with the present invention.

Referring now to the drawings, the flow chart of FIG. 3 describes a method of therapeutically closing or occluding a PFO 1. Generally, the treatment method involves inserting PFO treatment catheter 21 configured to transseptally deliver energy to the secundum 5 and the primum 7 to affect joining or welding of these tissues.

Figure 4A:
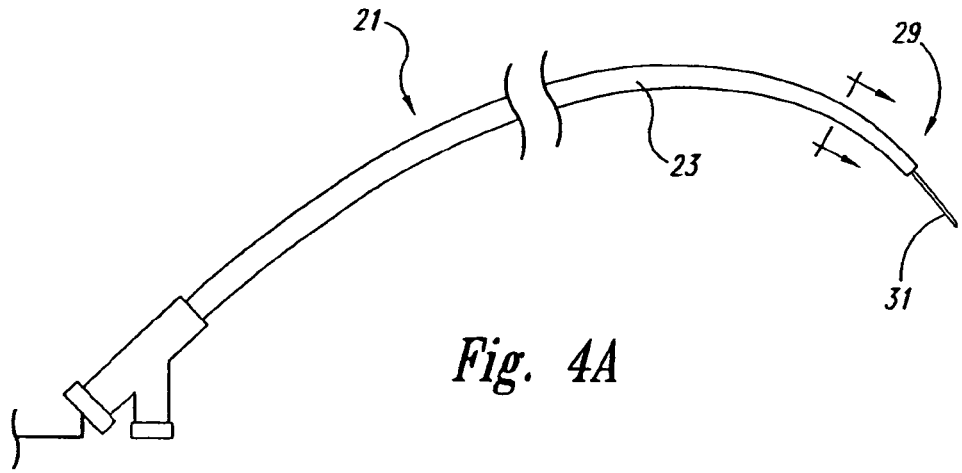
Figure 4B:
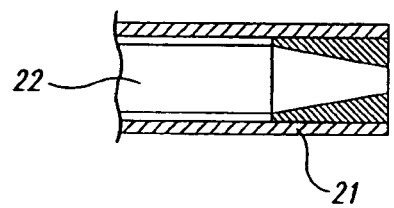

PFO treatment catheter 21, in accordance with the present invention is illustrated in FIG. 4A. PFO treatment catheter 21 should be long enough to extend from an insertion site to interatrial septum 3. Typical lengths for catheter 21 include, but are not limited to, a range of about 50°-200 cm and preferably sized between about 2-15 French. Suitable materials for PFO treatment catheter 21 include, but are not limited to, various polyethylenes, polyurethanes, polysilicones, other biocompatible polymers and materials well known to those skilled in the catheter arts. The interior 22 of catheter 21 is adapted to allow passage of one or more other catheters and components (such as guidewires 31, imaging devices, etc) therethrough. See FIG. 4B. PFO treatment catheter 21 can be further configured to comprise one or more lumens 22 extending its entire length or only a portion thereof. The one or more lumens 22 of catheter 21 can be used as paths for cables, other catheters, guidewire 31, pull wires, insulated wires, fluids, gases, optical fibers, vacuum channels, and any combination thereof.

PFO treatment catheter 21 can be used in conjunction with guidewire 31 so that it can be readily introduced and percutaneously advanced from the insertion site (such as a femoral vein, femoral artery, or other vascular access location) until distal working end 29 is appropriately seated within the patient's heart, at or near, PFO 1. In one possible implementation, guidewire 31 can be inserted into the femoral vein, advanced up the inferior or superior vena cava, into the right atrium and to the interatrial septum 3, near the fossa ovalis 10, and PFO 1.

Penetration of the interatrial septum 3 at a pre-determined location can be accomplished, with or without image guidance. Image guidance methods include but are by no means limited to: fluoroscopic; ultrasound (IVUS); intracardiac echo (ICE) ultrasound; magnetic resonance imaging (MRI); and echocardiographic guidance including transesophageal echocardiography (TEE). To penetrate and pass through interatrial septum 3, guidewire 31 can be removed and tissue penetrating device 41 advanced. In one embodiment of the present invention, tissue penetrating device 41 may be a puncturing needle such as conventionally available Brockenbrough needles or other like means. Another possible implementation involves the direct use of guidewire 31 to penetrate interatrial septum 3, eliminating the need to insert and advance separate tissue penetrating device or devices 41. In addition, various other transseptal penetrating methods and devices as disclosed in U.S. provisional applications: Ser. No. 60/447,760, filed Feb. 13, 2003 and entitled "PFO and ASD Closure via Tissue Welding" and Ser. No. 60/474,055, filed May 28, 2003 and entitled "Atrial Transseptal Atrial Access Technology" (the entire contents of which are hereby incorporated by reference and commonly assigned, and provided herein under separate headings) can also be used to affect penetration of interatrial septum 3 to facilitate the transseptal passage of various devices, including the distal end of PFO treatment catheter 21, into the left atrium of the heart.

Figure 5A:
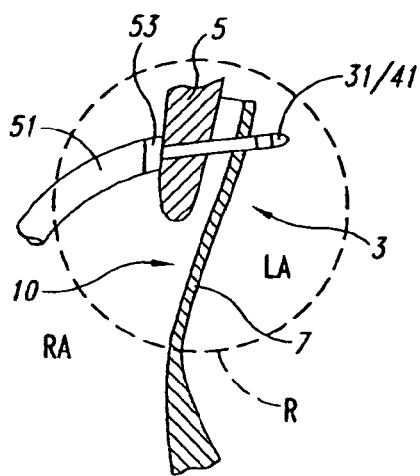
Figure 5B:
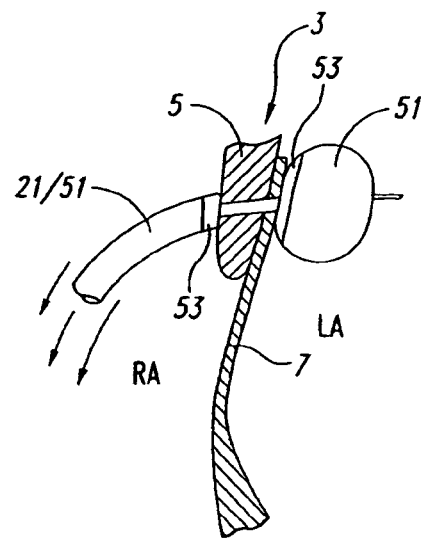

As illustrated in FIG. 5A, interatrial septum 3 can be punctured at a number of different locations within region R; however, for the purposes described herein, preferably, penetration of interatrial septum 3 is made at a location where secundum 5 and primum 7 overlap so that both tissue structures are penetrated. When septum 3 is penetrated, an access pathway is created allowing both secundum and primum to be encased between opposed members 51 and enabling access to the left atrium of the heart. As illustrated generally in FIG. 5B, opposed members 51 should be transseptally positioned inside the patient's heart before energy is delivered to the tissues. Opposed members 51 can be used as: (1) a means for coapting the tissues to be joined or welded; (2) a means for supplying compressive force to the tissues; and/or (3) a means for generating sufficient energy in order to heat the coapted tissues to a tissue temperature in a range between about 50°-100° C. One or more heat generating members 53 (for example, RF electrodes 53) can be disposed on opposed members 51 in order to affect tissue heating and application of therapeutic amounts of energy to the encased tissues. As described herein, other configurations are possible.

In the present invention, various energies, energy delivery sources and devices can be employed to increase the native tissue temperatures within a therapeutic range between about 50°-100° C. including: (i) a radiofrequency (RF) generating source coupled to one or more RF electrodes; (ii) a coherent or incoherent source of light coupled to an optical fiber; (iii) a heated fluid coupled to a catheter with a closed channel configured to receive the heated fluid; (iv) a resistive heating source and heating element; (v) a microwave source coupled to a microwave antenna; (vi) an ultrasound power source coupled to an ultrasonic emitter or from external ultrasound; or (vii) any combination of the above. Tissue heating by any of these methods should be tightly controlled to ensure no charring and prevent overheating of the surrounding cardiac tissues. Accordingly, various known temperature sensing means, tissue impedance monitoring techniques, feedback systems, and controls may be incorporated into the present invention and to PFO treatment catheter 21 to allow monitoring of the heating process. Various cooling techniques can be employed (such as the seepage or circulation of various biocompatible liquids, saline, or blood during the heating process as a cooling mechanism). Moreover, such heating systems can be made to focus more energy on the right side of the septum, so that any emboli that are generated will not be allowed to enter the systemic circulation.

For ease of discussion and illustration, and for the remainder of this invention, use of RF energy, in a range of about 100-1000 kHz, supplying power in a range of about 5-50 watts, for duty cycles in a range of about 0.5-20 seconds, will be discussed. The various heat generating members described below are either monopolar or bipolar RF electrodes 53. However, all of the other energy sources and devices described above are equally applicable and may be incorporated into any of the embodiments provided below and used to affect the transseptal joining or welding of tissues to partially or completely, close or occlude, a PFO.

Turning now to FIGS. 6-10 and 11, various embodiments of PFO treatment catheter 21 and catheter assemblies 21, for practicing the joining or welding treatment techniques of the present invention are described.

FIG. 6A illustrates one embodiment of PFO treatment catheter 21 in accordance with the present invention. PFO treatment catheter 21 comprises an elongated shaft having a proximal portion, a distal portion, a proximal inflation member 61, and a distal inflation member 63. Said proximal and distal inflation members 61, 63 are located at a distal working end 29 of catheter 21. Disposed on proximal 61 and distal 63 inflation members may be one or more RF electrodes 53 for tissue heating.

During use, guidewire 31 can be used to advance PFO treatment catheter 21 across and through interatrial septum 3 after interatrial septum 3 has been penetrated. Preferably, PFO treatment catheter 21 is advanced over guidewire 31 until distal inflation member 63 is located on the left atrial side of the interatrial septum 3 while proximal inflation member 61 is located on the right atrial side. To ensure this relative arrangement, these balloon structures 61, 63 can be inflated with contrast fluid, or one or more radio-opaque markers may be disposed on, or adjacent to, the inflation members, so that the desired transseptal positioning of the inflation members can be visually verified, for example, under fluoroscopy. After transseptal positioning of inflation members 61, 63 is visually verified, guidewire 31 may be removed and the tissue coapted together between proximal inflation 61 and distal inflation member 63. A simple method for coapting the tissues may be to expand the inflation members 61, 63 with a fluid (such as contrast solution); a gas (such as carbon dioxide), or any combination thereof. As shown in FIG. 6A, the secundum 5 and primum 7 should be transseptally encased between inflation members 61, 63.

Once coapted, the one or more RF electrodes 53 disposed on the surface of inflation members 61, 63 can be energized to heat the encased tissues and increase native tissue temperatures to about 50°-100° C. In accordance with this aspect of the invention, RF electrodes 53 should be disposed on the surface of the inflations member 61, 63 so that when inflated, these RF electrodes 53 are in direct contact with the tissues to affect efficient tissue heating. RF electrodes 53 can be energized as many times as needed to affect sufficient tissue heating and subsequently heat induced joining of the tissues. As illustrated in FIG. 6B, single monopolar RF electrode 53 can be disposed on the proximal inflation member 61 or alternatively a bipolar RF electrode 53 configuration may be used, wherein in a first electrode 53 is disposed on proximal inflation member 61 and second electrode 53 is disposed on distal inflation member 63. As will be readily appreciated by those skilled in the art, PFO treatment catheter 21 comprising a single monopolar electrode 53 on proximal inflation member 61 can be advantageous in that heating from the right atrial side of the septum 3 can potentially limit or eliminate the potential of any embolic material from being introduced into the systemic atrial circulation. RF electrodes 53 of this embodiment can be energized as many times and for as long as necessary to affect joining of the tissues. To adapt this embodiment of PFO treatment catheter 21 for the welding of the secundum 5 and primum 7, PFO treatment catheter 21 can be configured so that user applied force at the proximal end of PFO treatment catheter 21 is transmitted down elongated shaft 23, which then translates as compressive force supplied to the encased tissues by the proximal 61 and distal 63 inflation members.

RF electrodes 53 can be disposed on the surface of proximal 61 and/or distal 63 inflation members using techniques including: ion implanting, electroplating, sputtering, electro-deposition and chemical and/or adhesive bonding methods; to disposed various RF electrodes 53 on the surface of the proximal 61 and distal 63 inflation members. Electrodes 53 may be formed from gold, platinum, silver, or other materials, preferably, these other materials should be malleable, suitable for in-vivo tissue contact, and thermally conductive.

To verify that a satisfactory level of closure or occlusion has been achieved, contrast TEE, ICE or TCD bubble studies can be performed before catheter is withdrawn from the patient through the passage created during penetration of interatrial septum 3. Preferably, the opening should be small enough so that the body's natural injury response mechanisms will serve to close this left atrial access pathway. PFO treatment catheter 21 can be used in conjunction with a guide or introducer sheath or catheter to facilitate advancement of catheter 21 into and through the tortuous vasculature.

FIGS. 7A and 7B illustrate yet another embodiment of a PFO treatment catheter in accordance with the present invention. In this embodiment, secundum 5 and primum 7 are encased between distal end of PFO treatment catheter 21 and wire assembly 27. Wire assembly 27 can be pre-loaded into the distal working end 29 of catheter 21 and deployed by the user after puncture of the interatrial septum 3 in order to coapt the tissues.

FIG. 8 illustrates another embodiment of the present invention wherein PFO treatment catheter 21 comprised of two coiled RF electrodes 71, 73 disposed at the distal working end 29 of catheter 21. In this embodiment, coiled RF electrodes 71, 73 are pre-loaded inside PFO treatment catheter 21 and advanced out of distal working end 29 of catheter 21 by user applied pressure or force on a release element (not shown) located at the proximal end of catheter 21. As illustrated in FIG. 8, RF coils 71, 73 are transseptally deployable. The tissues are coapted by encasing them between RF coils 71, 73 that may be tension loaded. Alternatively, coiled RF electrodes 71, 73 may be disposed, for example on a wire or other like means, so that the user applied pull-back force on the wire serves to coapt and/or compress the tissues. Preferably, coiled RF electrodes 71, 73 should be made from any biocompatible material, including but not limited to: any nickel-titantium (Nitinol) alloy and other shape metal alloys, stainless steel, platinum, noble metals, and other like materials. Appropriate positioning of the RF coils 71, 73 may be visualized under fluoroscopy, x-ray, ultrasound, TEE, ICE, or using other conventional imaging techniques.

In this aspect of the invention, joining or welding of the tissues may be affected at a single tissue contact point; at multiple tissue contacts points; or alternatively along a seam in order to affect partial or complete closure of the PFO tunnel. To this end, RF coils 71, 73 may be configured with one or more selectively spaced RF electrodes 71, 73 disposed on the coiled surfaces of RF coils 71, 73 in order to create the desired tissue contact point, pattern or seam given a pre-selected size and shape.

Figure 9:
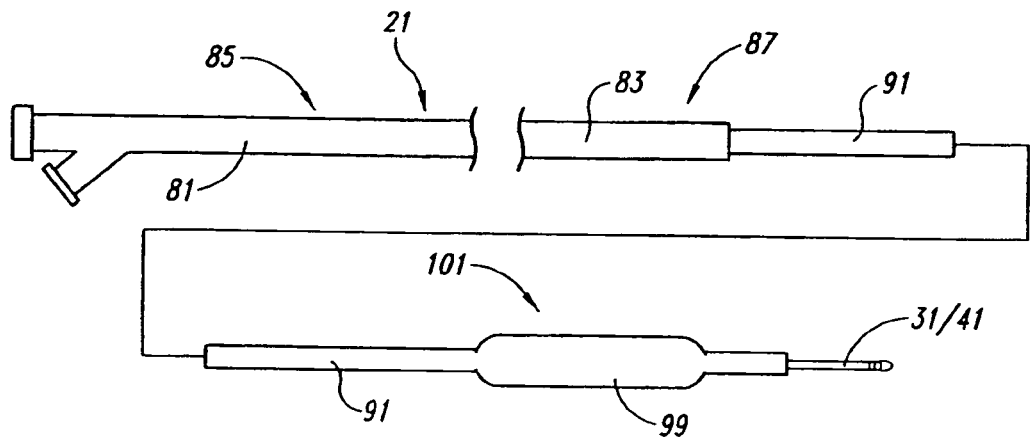
FIG. 9 is a perspective view of a PFO treatment catheter assembly comprising a guide catheter and an inflation catheter disposed within the guide catheter.

FIG. 9 illustrates yet another embodiment of present invention wherein a PFO treatment catheter assembly 21 is provided. As shown in FIG. 9, PFO treatment catheter assembly 21 is comprised of a guide catheter 81 and inflation catheter 91 disposed therein. As shown in FIG. 9, guide catheter 81 is comprised of an elongated shaft 83 having proximal 85 and distal 87 portion, and one or more lumens extending completely and/or partially therethrough with at least one lumen adapted to allow insertion and advancement of inflation catheter 91. Inflation catheter 91 is comprised of elongated inflation catheter shaft 93 having a proximal inflation catheter portion 95, a distal inflation catheter portion 97, one or more lumens extending completely or partially therethrough, and inflation member 99 located at a distal catheter working end 101.

During operation, guide catheter 81 should be disposed on the right atrial side while the distal working end of inflation catheter 101 is transseptally passed through until inflation member 99 is located on the left atrial side. Various tissue penetrating devices 41, as well as guidewires 31, can be used to facilitate the transseptal advancement of the distal working end of inflation catheter 101 into the left atrium (as well as insertion and advancement of guide catheter 81 to the interatrial septum 3). Once appropriately advanced, inflation member 99 can be inflated to coapt and encase the secundum 5 and primum 7 between distal end 89 of guide catheter 81 and inflation member 99. In one embodiment of the invention, one or more RF electrodes 53 can be disposed on distal end 89 of guide catheter 81 and on inflation member 99 located on the inflation catheter so that bipolar RF energy may be used to join or weld the tissues. In another embodiment, one or more monopolar RF electrodes 53 can be disposed on distal end 89 of the guide catheter 81 and energized. Once the energy delivery is completed, inflation member 99 may be deflated, and with inflation catheter 91 and guide catheter 81, withdrawn from the patient.

Figure 10:
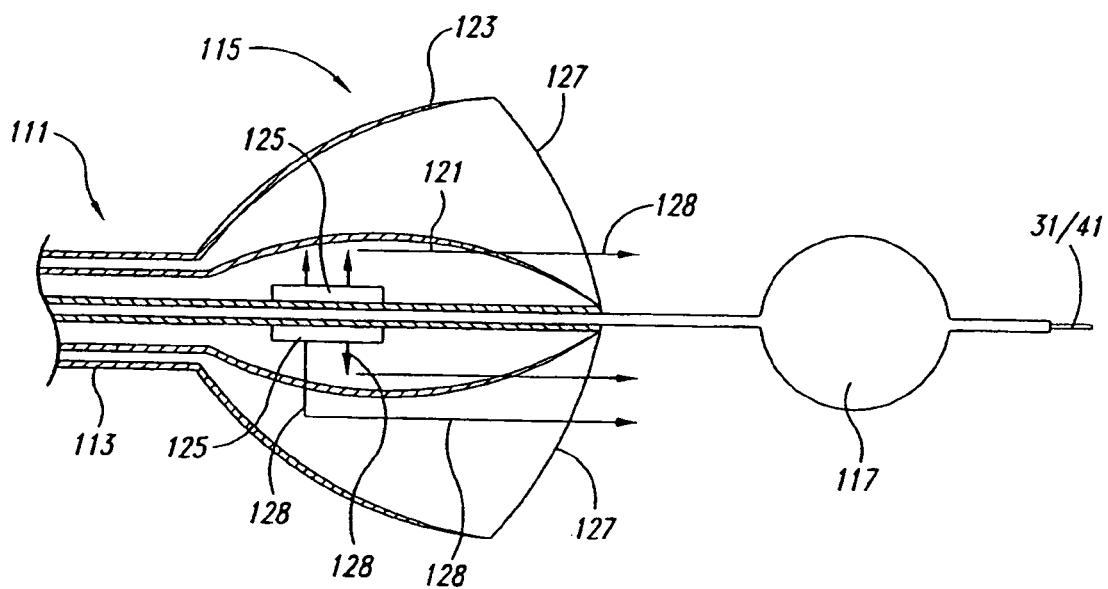
FIG. 10 illustrates yet another embodiment of a PFO treatment catheter comprises a high intensity ultrasound transducer.

FIG. 10 illustrates yet another embodiment of the present invention. In this embodiment, high intensity ultrasound catheter 111 as described in U.S. Pat. No. 6,635,054, the entire contents of which are hereby incorporated by reference and modified to suit the aims of the present invention, is employed to affect joining or welding of secundum 5 and primum 7 to close or occlude PFO 1.

As illustrated, the high intensity ultrasound catheter 111 is comprised of catheter shaft 113, first balloon 115, and gas-filled second balloon 117 located at distal working end of catheter 111. Comprised within first balloon 115 is gas filled inner "structural" balloon 121 and liquid filled outer "reflector" balloon 123, which is coaxially disposed around the inner structural balloon such that when both structural 121 and reflector 123 balloons are in a deflated configuration, reflector balloon 123 closely overlies deflated structural balloon 121. As shown in FIG. 10, disposed within the inner structural balloon 121 is ultrasound transducer 125 adapted to emit high intensity ultrasound energy.

In use, a high intensity ultrasound catheter 111 is positioned so that first balloon 115 is disposed within right atrium and second balloon 117 is disposed within the left atrium. Once appropriately positioned, first 115 and second 117 balloons may be inflated and the tissues to be joined or welded, coapted between first 115 and second 117 balloon. Ultrasound transducer 125 located within first balloon 115 is energized and acoustic energy projected forward into the tissues coapted between the two 115, 117 inflated balloons.

Because second balloon 117 is gas filled (and because high intensity acoustic waves cannot and do not travel well in gases) second balloon 117 functions to reflect any excess energy, preventing overheating in the left atrium and minimizing the risk of left side embolic events.

Briefly, the forward projection of acoustic energy from ultrasound transducer 125 into the coapted tissues is achieved by the configuration and shape of gas-filled structural balloon 121 and fluid filled reflector balloon 123 within first balloon 115, as described in more detail in U.S. Pat. No. 6,635,054. As described therein, gas-filled structural balloon 121 is comprised of active wall 127 which is formed from a flexible material and has a specific shape or configuration (parabolic or conical shape) when inflated. The shape of active wall 127, in conjunction with air-filled reflector balloon 123, functions to refract and project the acoustic waves 128 generated by the ultrasound transducer distally forward as illustrated in FIG. 10. Once sufficient energy is applied, first 115 (including structural 121 and reflector 123 balloons) and second 117 balloons are deflated and withdrawn through the access pathway created when interatrial septum 3 is penetrated.

Figure 11A:
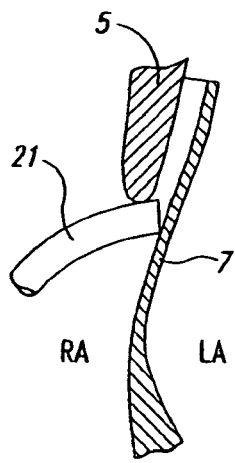
FIGS. 11-12 illustrate various biocompatible, atraumatic, implantable mechanical devices for the transseptal occlusion or closure of a PFO.
Figure 11B:
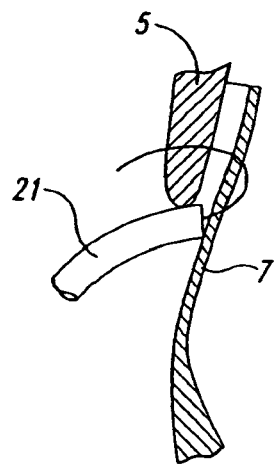
Figure 11C:
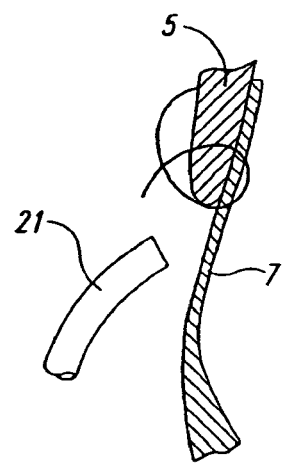
Figure 12A:
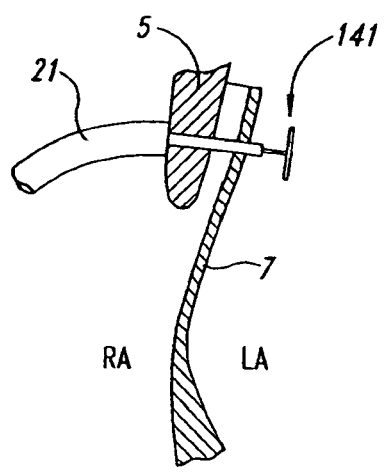
Figure 12B:
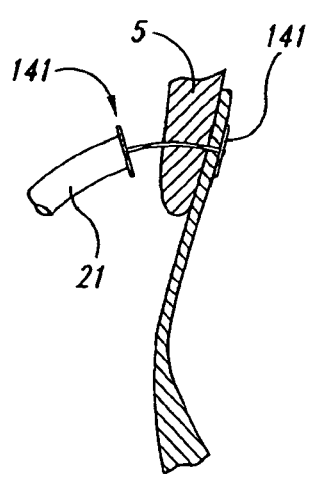
Figure 12C:
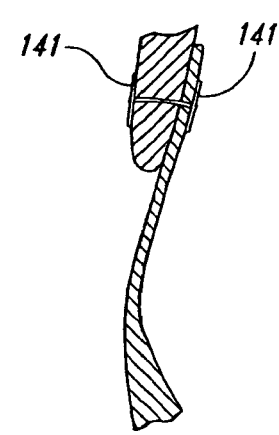
Figure 13A:
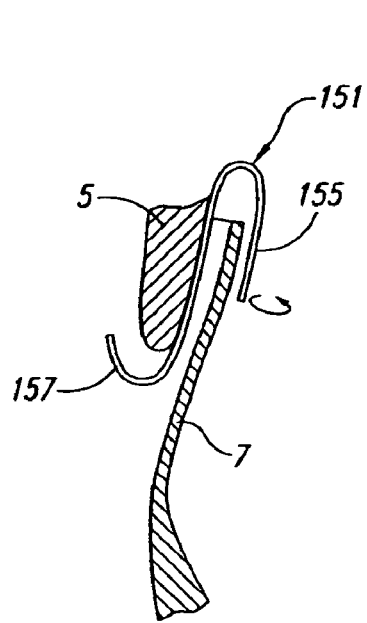
FIGS. 13A-13E illustrate a hook-and-twist mechanical device for occluding or closing a PFO in accordance with this aspect of the invention, where.
Figure 13B:
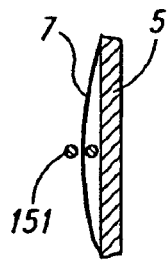
Figure 13C:
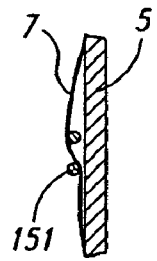
Figure 13D:
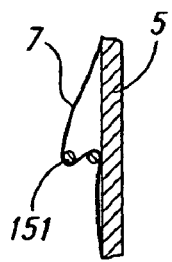
Figure 13E:
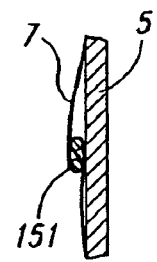

FIGS. 11-12 are diagrammatic representations of yet another aspect of the present invention wherein devices 141 adapted for the efficient occlusion or closure of a PFO are shown. In accordance with the present invention, these devices 141 include various clips, staples, T-bar, Z-part devices that can be transseptally deployed. Preferably, such devices 141 should be formed from biocompatible materials such as various nickel-titanium and other shape memory alloys, stainless steel, platinum and other like materials. Preferably these devices 141 should not require the subsequent device endothelization, but rather should result in immediate, partial or complete, closure or occlusion of a PFO by coapting secundum and primum. Devices 141 can be delivered and deployed, however, a further implementation of this aspect of the invention, is devices 141 being heat secured after delivery. As will be readily appreciated by those skilled in the art, one fairly significant issue related to use of heat generating members (such as RF electrodes) is that heated tissue frequently adheres or sticks to the member. (For further discussion of this issue, please refer to U.S. Pat. No. 4,492,231, the entire contents of which are hereby incorporated by reference.) While this may pose technical difficulties in other circumstances, this embodiment of the invention utilizes this feature to ensure that the coapted tissues and devices 141 are securely heat fixed together and implanted in the patient to avoid or prevent device migration, dislodgement, etc. Accordingly, various devices 141 can be configured to comprise one or more RF electrodes using monopolar or bipolar RF energy to affect heat attachment of devices 141.

FIGS. 13A-13E illustrate yet another aspect of the present invention referred to herein as "hook-and-twist" device 151. Hook-and-twist device 151 shown in FIG. 12 is comprised of an elongated neck 153 disposed between proximal hook 155 and distal hook 157. As illustrated in FIG. 12 and unlike the other devices illustrated in FIG. 11, "hook-and-twist" device 151 of this embodiment is advanced into and through the tunnel-like opening of the PFO 1. The proximal and distal hooks 155, 157 are designed to atraumatically engage and catch PFO 1 from the right and left atrial sides of PFO from within the PFO tunnel or PFO opening. To implant device 151, it is wound until the tissues engaged by device 151 are squeezed together and become taunt; and the increased tautness in the tissues serves to decrease the likelihood of PFO 1 from opening. In this embodiment, after device 151 has been appropriately twisted, device 151 would be disengaged from a delivery catheter and thus implanted. In a related but different embodiment, hook-and-twist device 151 and the tissues encased in by hook-and-twist device 151 can be configured to comprise one or more monopolar electrodes to affect welding of the encased tissues and heat attachment of implanted device 151 inside the patient.

As discussed above, sticking of heated tissues to the various heating elements 53, RF coils 71, 73, etc. should be avoided in those non-implant embodiments of the present invention. To this end, several techniques can be employed. For instance, various non-adhesive biocompatible gels, hydrogels, liquids (such as saline) may be employed to facilitate the release of the heated tissues from various PFO treatment catheters 21 of the present invention. Preferably, such materials are bio-absorbable. Also, these materials should be electrically conductive when used in conjunction with RF energy based components creating a complete electrical circuit. These materials may be disposed on the external surface of catheter 21 or extruded from one or more ports disposed at or near the distal ends of the various devices (coils 71, 73, balloons 61, 63) and catheters 21 of the present invention. In accordance with this aspect of the invention, inflation members 61, 63 may be formed of porous material in order to facilitate seepage of saline or other like liquids to the tissues being heated. This seepage facilitates char-fee heating, ready release of tissues from the heating elements, and/or completion of the electrical circuit to enhance and promote the energy delivery process. In addition, circulation of these materials (as well as blood and/or other biological fluids) can also be provided as a means to promote cooling and heat dissipation during the energy delivery process to prevent issues of overheating, tissue charring, etc.

Figure 14A:
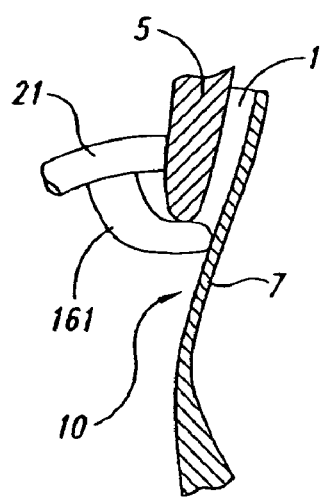
FIG. 14 generally illustrate yet another aspect of the present invention wherein the various PFO treatment catheters and device can be adapted with a location member designed to facilitate detection and location of a PFO, puncture location, as well as maintains the position of the PFO treatment catheter during the treatment process.
Figure 14B:
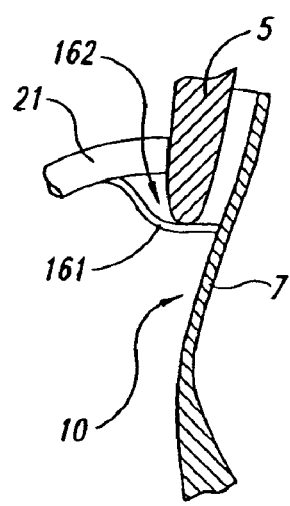
Figure 18A:
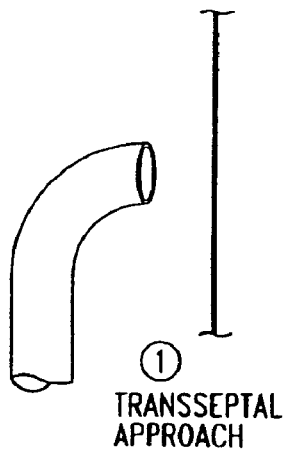
Figure 18B:
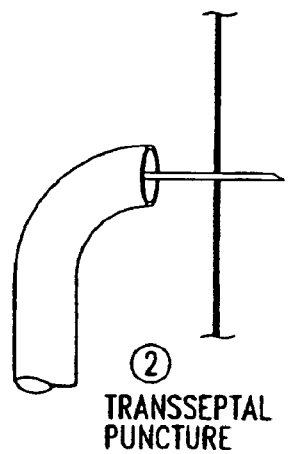
Figure 18C:
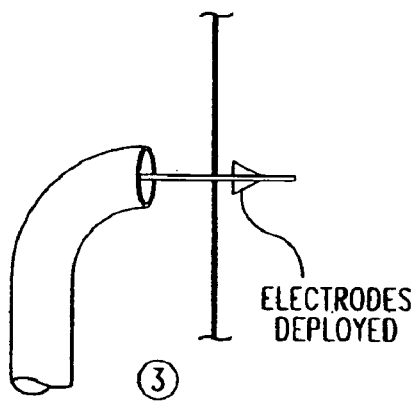
Figure 18D:
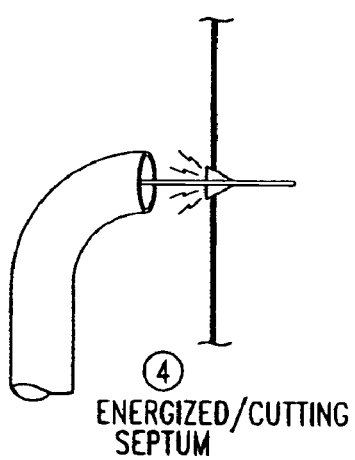
Figure 19A:
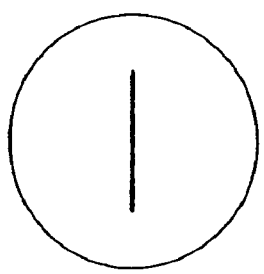
Figure 19B:
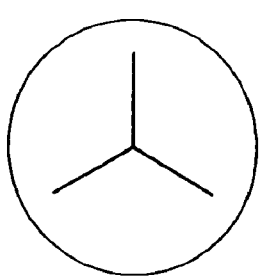
Figure 19C:
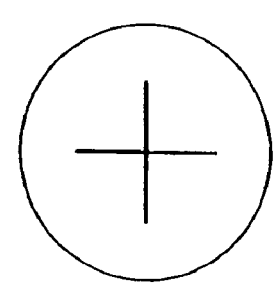
Figure 20A:
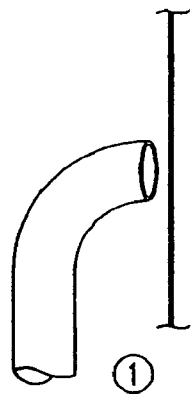
Figure 20B:
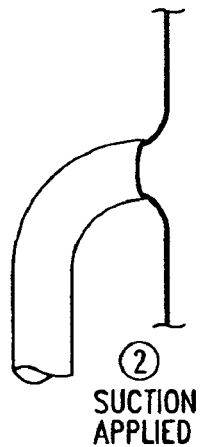
Figure 20C:
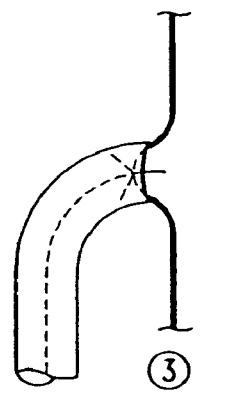
Figure 20D:
Figure 21A:
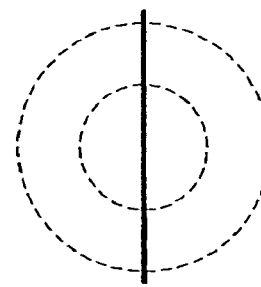
Figure 21B:
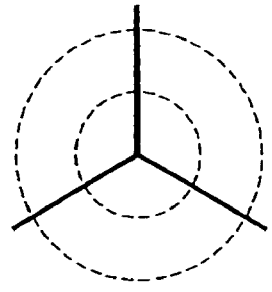
Figure 24A:
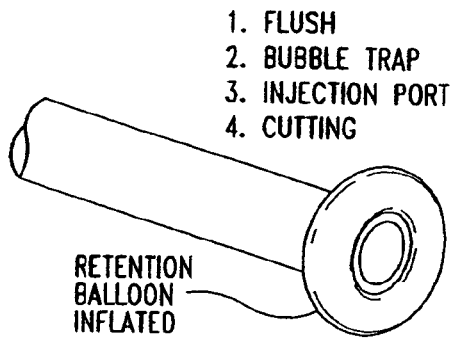
Figure 24B:
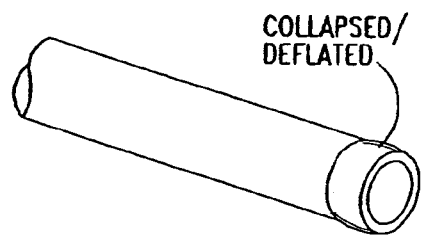
Figure 25:
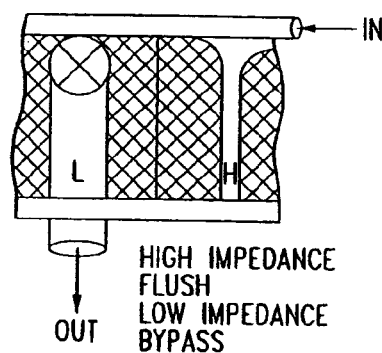
Figure 26:
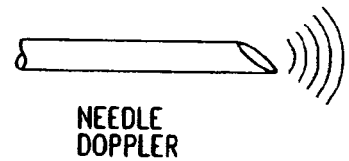
Figure 27:
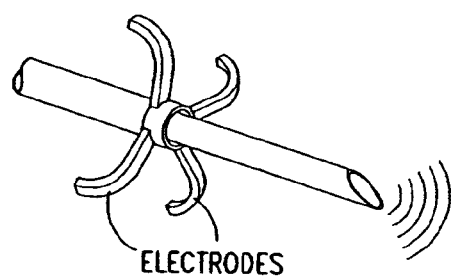
Figure 28:
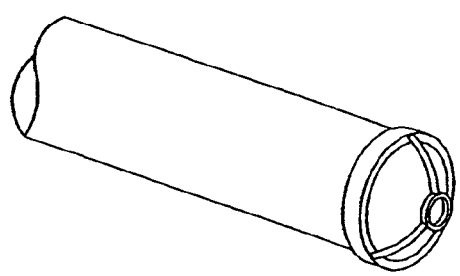

Detecting and locating PFO 1 is an important aspect of the invention and conventional techniques, including ultrasound, fluoroscopy, TEE, ICE, and ear oximetry techniques can be used for this purpose. In yet another embodiment, of the present invention the various catheters 21 of the present invention can be adaptively shaped to identify and engage certain detectable anatomical structures (such as the annular structure surrounding the fossa ovalis 10) as one means of locating PFO 1 as well as securely positioning PFO treatment catheters 21 and catheter assemblies 21 for penetration of interatrial septum 3 and the energy delivery process. In one embodiment, the various catheters 21 may be configured to further comprise location means 161 complementarily shaped to securely engage the antero-superior portion of the annular tissue structure 162 that typically surrounds the fossa ovalis 10 which is near PFO 1; or location means 161 may alternatively be used to locate the fossa ovalis 10. This aspect of the invention is illustrated in FIG. 14.

In a further aspect of the present invention, the process of joining or welding of the tissues can be immediate leading to PFO 1 closure or occlusion following energy delivery in accordance with the present invention. However, it is also contemplated that joining or welding of the tissues can occur over several days wherein the tissue joining process is mediated in part to the body's healing response to thermal injury. Nevertheless, whether the closure or occlusion of the PFO is immediate or gradual, complete or partial; preferably, the attachment of the primum and secundum to affect PFO 1 closure or occlusion should be permanent.

A. Closure of Patent Foramen Ovale Via Tissue Welding

This disclosure describes a method to close a probe patent foramen ovale using a concept of electrical "spot welding" of the tissue planes together. This may be achieved by placing a clamp device across the atrial septum that contains electrodes. These electrodes are energized with an appropriate energy source, and momentarily melt the collagen tissue of the valve together. This is, in effect, a spot-weld of the tissue without the need for an implantable device. The overlap of the septae are welded together at spots of the high temperature.

The technique may also entail a prosthetic membrane that can be melted with the high temperature of the electrical energization. This then becomes an integral part of the tissue, as tissue grows into the membrane to make a hybrid biologic/polymer structure.

B. PFO, Latrogenic Transseptal Atrial Septal Defect Closure and Closing it Patent Foramen Ovale via Tissue Welding This disclosure is an addendum describes a method to 1) create a safe ASD for transseptal access, and also its closure.

The concept builds on a prior disclosure for closing probe patent foramen ovale lesions using "spot welding" of the tissue planes together.

Atrial Septal Access: Making a Slit/Series of Slits in a Defined Pattern

The first technology is a device and method for using a cohort of electrodes which are collapsed, placed across the atrial septum, (for example over a guidewire) expanded and energized. The design of the electrodes may be such that they can cut in either a forward direction ("push"), or designed to cut retrograde ("pull"). The device is placed against the septum, the electrodes contact tissue, the electrodes are energized, and the tissue is immediately cut. This may take the form of a single slit, a triangle, a "Mercedes Benz" symbol or any other pattern. The electrodes may be a collection of expandable wires. The device may be monopolar, or have a backing plate and so be a bipolar system. A wire can cross the atrial septum first, the device is low profile and brought through. The electrodes may be collapsible in any manner, and the size of lesion/slits made may be of any pattern. The device is removed over the guidewire, which is left in place. A skive configuration for "rapid exchange" may be used in the catheter access to facilitate operator interaction. Three of many possible cutting patterns are illustrated in FIGS. 15A-15C.

Atrial Septal Closure: Closing the Lesion when the Procedure is Complete

Closure is accomplished in a similar manner. The septum is crossed with a pre-existing wire. An electrode of any appropriate sealing or welding pattern is brought to the site with a return electrode. The septum may or may not be clamped between electrodes, the electrodes energized with a coagulation waveform. This seals the lesion in place, and permits the body's healing mechanisms to heal along the cut surfaces. The pattern may be, for example, one or more circles that progressively leave a lesion making the overall hole less able to move with pressure. These are illustrated in FIGS. 16A-16C with the dotted line indicating circles of coagulation lesion formation.

FIG. 17 shows a dual-membrane with a slice, and a coagulating, circular lesion.

In an additional iteration, suction is applied to bring the septal membrane into contact with either a sharp cutting blade set, or an electrode set that can be energized to cut the lesions in the septum. Embodiments are shown in FIGS. 18-23.

C. PFO, Iatrogenic Transseptal Atrial Septal Defect Closure, Mitral Annulus Shrinkage via Tissue Welding and Lesion Induction This disclosure is an addendum describing an additional method for closing the patent foramen ovale. The purpose of this addendum is to describe the use of a burn lesion that induces chronic wound contraction. The pattern of the burn induces the contraction as fibrosis occurs.

The solution entails a pattern of lesion generated by an electrical burn in the atrial septal tissue. The electrical burn can be made as a bipolar lesion, to span, for example the area of the lesion. The pattern of the burn can be such that the healing generates fibrosis, and the fibrosis results in wound contraction that closes the lesion.

This is also useful for shrinking the Mitral valve annulus. The lesions cause chronic contraction. They may be made in the coronary sinus, or in the annular ring itself.

They may also be made on the surface of the aorta to prevent aneurysms from growing larger.

The lesions cause wound contraction, and thus "negative remodeling." Embodiments are shown in FIGS. 24A-32C.

A. Atrial Transseptal Access Technology

General

This disclosure describes a method to cross the atrial septum as techniques requiring transseptal access become more prevalent. In this disclosure the device has the capability of a rapid, precise, and controlled incision of the atrial septum for transseptal catheter delivery.

Cutting and Electrodes

The device is a catheter, and the method of cutting the septal tissue is with RF or electrosurgical energy. This permits using non-sharp objects within the heart, energized only when desired, and little chance for injury of myocardial, conduction, valvular, and other important tissue. The electrodes performing the cutting are wires, partially insulated. These wire electrodes can expand, constitute an expandable electrode system, as in a wire pattern, that contacts the atrial septal tissue of interest. The system is delivered as a catheter, expands at the site of the atrial septum.

The electrodes may be compressed or expanded longitudinally to bring them into position, or they may be self-expanding/positioning. They may reside within the catheter and by operator action of pushing or pulling leave the catheter to form themselves into the proper position. In this configuration the electrodes may have spring potential and can themselves utilize the necessary spring action for cutting when energized. Any number of patterns may be formed, such as sectors of circles with 1, 2, 3, 4 or more cuts by the electrodes. The electrodes may be concentric, and so incorporated into a delivery catheter having a lumen for needle, fluid, balloon or other device delivery. The needle may be used to punch through the septum initially, and anchor the catheter in place, allowing the electrode device to be brought into place concentrically with the needle. Following energization and cutting, the catheter containing the electrodes is advanced across the septum, the needle removed, and guidewire replaces the needle.

Electrodes

The wires may be insulated on one side, that side not contacting the septal tissue. The system uses electrical energy, typically RF cutting current, so all tissue in contact with the electrode surface is cut.

Spring-Loading

The device may be spring-loaded, so that it may travel only a finite length after it has been energized and cutting occurs. The purpose of spring-loading is that a small, fixed distances. The device is pushed or pulled, to load the spring-action and put the electrodes firmly in contact with the septal tissue. The electrodes are then energized, and the cutting happens rapidly, leaving a pattern of the cut in the shape of the electrode/electrodes. The cutting electrode energization may be monopolar or bipolar.

Catheter

The device may be pushed or pulled, following crossing of the septal membrane/tissue by a guidewire.

A skive the needle rides in, pull the needle and a guidewire is waiting in place to advance from another skive. The guidewire is pulled out. A "stop" on the guidewire, cannot be retrogradely removed from the catheter/skive.

Suction

The device may have a suction apparatus that immobilizes the atrial septal tissue. The suction may also pull it against the electrodes, or may pull it positively against the electrode system. The device has a fluid delivery port that may be used to deliver saline, water, or other liquids to the cutting site. The purpose of the fluid is to provide insulation, or possibly a high-impedance solution at the site.

Other Capabilities

The system has a capability of measuring electrical impedance of the object in contact with the electrodes, so that contact with the septum can be determined through an impedance measurement. This electrode system can also be used to measure an electrocardiographic or other bio-electric signal within the heart.

Doppler Tip

The device has an integral ultrasound transducer. It may be imaging and/or Doppler (Pulsed Wave/Continuous Wave). This permits imaging of the site, or an audible signal of the flow distal to the probe.

A signal also may be emitted from this transducer to appear on an external TTE or TEE, or MRI localization in real-time.

B. Atrial Transseptal Access Technology (Continued)

General

This disclosure describes a method to cross the atrial septum as techniques requiring transseptal access become more prevalent. In this disclosure the device has the capability of a rapid, precise, and controlled incision of the atrial septum for transseptal catheter delivery.

Wire Cutting Electrode

It performs this function using a spring concept for the wire electrode. The wire is in a cage-like configuration to make the incision when electrified with the appropriate current configuration.

Spring Action of the Electrode for Current Density Enhancement

The device is pressed against a structure such as the interatrial septum, which compresses the spring in a non-uniform fashion. The compression required is not so intense as to risk perforating the thin structure such as the atrial septum. The contact point is thus limited to a small region of the electrode, which moves as the device sequentially cuts through the septum. This permits greater current density and thus cutting efficiency. The device sequentially cuts through the structure of interest as it continues to expand. The rear portion of the device may be insulated to further concentrate current at the cutting point of interest. When fully expanded, the device has traveled a defined distance only, by the spring expansion. This then permits safety since it cannot go farther than the expanded spring distance.

The spring may also be located distal to the tip and cutting system, with or without the spring configuration of the electrodes. The electrodes may also be mounted on a rigid or semi-rigid structure.

Pointed Tip to Stabilize the Device Prior to Activation

The spring may have a pointed tip or tips, or another tip configuration that permits grasping the septal tissue to stabilize the device in preparation for electrification and cutting.

Hole In The Tip for Guidewire, Small Catheter, or Needle Placement

The distal tip of the device may have a hole in it, to receive a guidewire, a working needle, or a catheter for injection. Any of these three components may be used to stabilize the device at any time during the incision process.

In the case of the spring-like activity, a floating collar is disclosed that slides over the needle/catheter/guidewire.

Guiding Catheter and Components

Balloon Inflation on Tip for Anchoring in Septum

The guide catheter has a doughnut-shaped balloon around the outside of the guide. It is inflated to permit anchoring-in-place.

The device may have prongs to exit and support the catheter placement.

High-Impedance, High-Pressure, Low-Flow Valve

The device has a specialize auto-flush valve that provides a continuous low flow, but high impedance and high pressure source. This is achieved as disclosed in other intellectual property. There is a spring-loaded, manual bypass for high flow that is manually activated. These features keep a positive pressure, low flow Pressure Activated Access Valve Disclosed in another issued patent.

Bubble Trap

A bubble trap capable of filtering micro- and macro-bubbles out of the fluid line is disclosed. The filtering mechanism consists of a microporous hydrophobic membrane. An air-relief/air withdrawal valve, auto-actuating is on this system.

Drug Injecting Port

An auto activating drug injection port is available to inject drug into the catheter. The valve is entered by a syringe and opened by the syringe. It is automatically closed as the syringe is withdrawn.

Pressure Transducer

Built-in pressure transducers are present for measurements of pressure. The needle may also be used as a fluid column to measure pressures at its tip.

Doppler Tip

The device has an integral ultrasound transducer. It may be imaging and/or Doppler (Pulsed Wave/Continuous Wave). This permits imaging of the site, or an audible signal of the flow distal to the probe.

A signal also may be emitted from this transducer to appear on an external TTE or TEE, or MRI localization in real-time.

Finally, while several particular embodiments of the present invention have been illustrated and described, it will be apparent to one of ordinary skill in the art that various modifications can be made to the present invention, including one aspect of one embodiment combined with another aspect of one embodiment. Other obvious adaptations of the present invention include the use of the devices, methods, and systems during minimally invasive surgery.

Also, as will be readily appreciated by those skilled in the art, the present invention described methods and devices that can be used to treat other types of cardiac defect. The general energy-based method for joining tissues is applicable as a therapeutic treatment method for closing other cardiac defects including, but not limited to patent ductus arteriosus, atrial septal defects, and other types of abnormal cardiac openings wherein an effective treatment is to join or weld tissue. Accordingly, the present invention and the claims are not limited merely for the therapeutic treatment of PFO but can be used for closure of occlusion of cardiac defects, body lumens, vessels, etc. Modifications and alterations can be made without departing from the scope and spirit of the present invention and accordingly, it is not intended that the invention be limited, except as by the appended claims.

What is claimed is:

1. A method for closing a patient's patent foramen ovale, comprising:
    drawing at least one of the patient's primum and secundum toward the other, the primum and the secundum being portions of the patient's atrial septum;
    applying energy to the primum and secundum; and
    fusing at least a portion of the primum and a portion of the secundum together to at least partially seal the patent foramen ovale.

2. The method of claim 1 wherein fusing includes fusing at a first location of the atrial septum, and wherein the method further includes fusing at least one additional location of the atrial septum.

3. The method of claim 1 wherein fusing includes spot welding the atrial septum.

4. The method of claim 1 further comprising at least partially sealing the patent foramen ovale without leaving an implantable sealing device in the patient's heart.

5. The method of claim 1 wherein applying energy includes applying RF energy.

6. The method of claim 1 wherein applying energy includes applying sonic energy.

7. The method of claim 1 wherein drawing at least one of the patient's primum and secundum toward the other includes clamping the primum and secundum between a first electrode and a second electrode.

8. The method of claim 1 wherein fusing the tissue includes melting the tissue.

9. The method of claim 1, further comprising applying a vacuum to bring atrial septal tissue into contact with an electrode.

10. The method of claim 1 wherein applying energy to the primum and the secundum includes shrinking at least one of the primum and the secundum.

11. The method of claim 1 wherein fusing the tissue includes fusing the tissue acutely.

12. The method of claim 1 wherein fusing the tissue includes fusing the tissue acutely to at least partially seal the patent foramen ovale, and wherein the method further comprises allowing the patient's healing process to further seal the patent foramen ovale.

13. A method for closing a patient's patent foramen ovale, comprising:
    applying a vacuum to the patient's atrial septum, the atrial septum including a primum and a secundum;
    applying energy to the primum and secundum; and
    fusing at least a portion of the primum and a portion of the secundum together to at least partially seal the patent foramen ovale.

14. The method of claim 13 wherein fusing includes fusing at a first location of the atrial septum, and wherein the method further includes fusing at least one additional location of the atrial septum.

15. The method of claim 13 wherein fusing includes spot welding the atrial septum.

16. The method of claim 13, further comprising at least partially sealing the patent foramen ovale without leaving an implantable sealing device in the patient's heart.

17. The method of claim 13 wherein applying energy includes applying RF energy.

18. The method of claim 13 wherein fusing the tissue includes melting the tissue.

19. The method of claim 13 wherein applying energy to the primum and the secundum includes shrinking at least one of the primum and the secundum.

20. The method of claim 13 wherein fusing the tissue includes fusing the tissue acutely.

21. The method of claim 13 wherein fusing the tissue includes fusing the tissue acutely to at least partially seal the patent foramen ovale, and wherein the method further comprises allowing the patient's healing process to further seal the patent foramen ovale.

22. A method of treating a patent foramen ovale in a heart, the method comprising:
    advancing a catheter device for treating the patent foramen ovale to a position in the heart which does not extend through the patent foramen ovale; and
    applying energy to tissues adjacent the patent foramen ovale with the catheter device to substantially close the patent foramen ovale.

* * * * *